United States Patent
Michaud et al.

(10) Patent No.: US 11,834,429 B2
(45) Date of Patent: Dec. 5, 2023

(54) MONOETHYLENICALLY UNSATURATED MONOMERS AND USES THEREOF

(71) Applicants: BOSTIK SA, Colombes (FR); CENTRE NATIONAL DE LA RECHERCHE SCIENTIFIQUE, Paris (FR); UNIVERSITE DE RENNES 1, Rennes (FR)

(72) Inventors: Guillaume Michaud, Venette (FR); Stéphane Fouquay, Venette (FR); Frédéric Simon, Venette (FR); Cyril Chauveau, Rennes (FR); Sophie Guillaume, Vitre (FR); Jean-François Carpentier, Acigne (FR)

(73) Assignees: BOSTIK SA, Colombes (FR); CENTRE NATIONAL DE LA RECHERCHE SCIENTIFIQUE, Paris (FR); UNIVERSITE DE RENNES 1, Rennes (FR)

( * ) Notice: Subject to any disclaimer, the term of this patent is extended or adjusted under 35 U.S.C. 154(b) by 554 days.

(21) Appl. No.: 17/058,197

(22) PCT Filed: May 29, 2019

(86) PCT No.: PCT/FR2019/051267
§ 371 (c)(1),
(2) Date: Nov. 24, 2020

(87) PCT Pub. No.: WO2019/229384
PCT Pub. Date: Dec. 5, 2019

(65) Prior Publication Data
US 2021/0179576 A1    Jun. 17, 2021

(30) Foreign Application Priority Data
May 31, 2018    (FR) ...................... 1854689

(51) Int. Cl.
| | | |
|---|---|---|
| *C07D 317/40* | (2006.01) |
| *C08F 212/08* | (2006.01) |
| *C08F 220/14* | (2006.01) |
| *C08F 220/28* | (2006.01) |
| *C08F 220/18* | (2006.01) |

(52) U.S. Cl.
CPC .......... *C07D 317/40* (2013.01); *C08F 212/08* (2013.01); *C08F 220/14* (2013.01); *C08F 220/283* (2020.02); *C08F 220/1804* (2020.02); *C08F 220/1811* (2020.02)

(58) Field of Classification Search
CPC .. C07D 317/40; C08F 220/283; C08F 220/40; C08F 220/1804; C08F 220/1811; C08F 213/08
See application file for complete search history.

(56) References Cited

U.S. PATENT DOCUMENTS

| | | | |
|---|---|---|---|
| 3,020,290 A | 2/1962 | Moss | |
| 5,240,835 A | 8/1993 | Pettrone et al. | |
| 10,723,836 B2 * | 7/2020 | Michaud ................ | C08G 71/04 |
| 2010/0291640 A1 | 11/2010 | Stuermer et al. | |
| 2015/0315310 A1 | 11/2015 | Michaud et al. | |

FOREIGN PATENT DOCUMENTS

| | | |
|---|---|---|
| DE | 102009003035 A1 | 11/2010 |
| EP | 0078413 A1 | 5/1983 |
| JP | 2015108809 A | 6/2015 |
| WO | 9602253 A1 | 2/1996 |
| WO | 200405088 A1 | 1/2004 |
| WO | 2013144299 A1 | 10/2013 |
| WO | 2014091173 A1 | 6/2014 |

OTHER PUBLICATIONS

ISA/EP; International Search Report and Written Opinion for International Patent Application No. PCT/FR2019/051267 dated Sep. 11, 2019, 11 pages.

* cited by examiner

*Primary Examiner* — Timothy R Rozof
(74) *Attorney, Agent, or Firm* — NK Patent Law

(57) ABSTRACT

The invention relates to a monoethylenically unsaturated monomer of formula (I), and to the use thereof for producing a polymer. The invention also relates to the polymer obtained by polymerising said monomer, and to the use thereof in a composition for producing coatings.

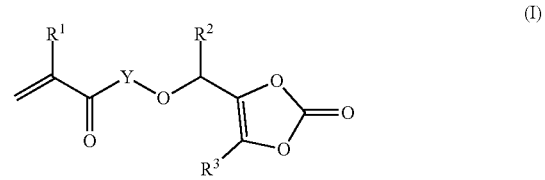

(I)

15 Claims, No Drawings

MONOETHYLENICALLY UNSATURATED MONOMERS AND USES THEREOF

CROSS-REFERENCE TO RELATED APPLICATIONS

This application is a U.S. National Stage application of International Patent Application No. PCT/FR2019/051267, filed on May 29, 2019, which claims the benefit of French Patent Application No. 1854689, filed on May 31, 2018.

FIELD OF THE INVENTION

The present invention relates to monoethylenically unsaturated monomers comprising at least one reactive function.

The present invention also relates to the use of said monomers for preparing polymers, and also to the compositions comprising said polymers.

Finally, the present invention also relates to the use of crosslinkable compositions.

TECHNOLOGICAL BACKGROUND

Polymers of acrylic or methacrylic type containing repeating units based on glycerol carbonate are known. These polymers are used in particular with amino compounds to prepare crosslinkable compositions for the production of coating materials. However, these polymers are typically reactive at high temperature (about 80° C.), and have low reactivity at room temperature.

There is therefore a need to provide new monomers that enable the preparation of polymers having improved reactivity compared to existing polymers.

There is also a need to provide novel multicomponent compositions having satisfactory adhesion properties and/or mechanical performance.

DESCRIPTION OF THE INVENTION

Monomers

The present invention relates to a monoethylenically unsaturated monomer M comprising at least one function of formula (A) below:

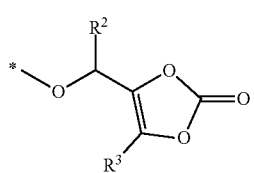

(A)

wherein:
$R^2$ represents a hydrogen atom, a linear or branched alkyl radical comprising from 1 to 10 carbon atoms, a cycloalkyl radical comprising from 3 to 10 carbon atoms, an aryl (preferably phenyl) radical or an arylalkyl (preferably phenylalkyl) radical;
$R^3$ represents a hydrogen atom, a linear or branched alkyl radical comprising from 1 to 10 carbon atoms, a cycloalkyl radical comprising from 3 to 10 carbon atoms, an aryl (preferably phenyl) radical or an arylalkyl (preferably phenylalkyl) radical;
or $R^2$ and $R^3$ may be bonded together to form a $-(CH_2-)_p-$ group with p being an integer ranging from 3 to 5.

Preferably, the monoethylenically unsaturated monomer M comprises at least one function of formula (A'):

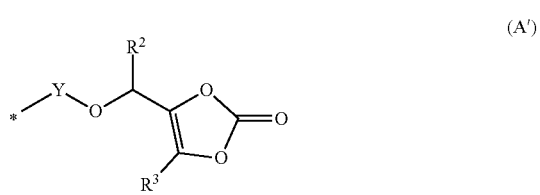

(A')

$R^2$ and $R^3$ are as defined above; and
Y represents a bond or a $-X_1-(CH_2)_n-X_2-$ radical with:
  $X_1$ represents O, S, NH or NR' with R' representing an alkyl radical preferably comprising from 1 to 6 carbon atoms, $X_1$ preferably representing O;
  $X_2$ represents NHC(O) or C(O), $X_2$ preferably representing NHC(O);
  n represents an integer ranging from 2 to 10, preferably from 2 to 10, preferentially from 2 to 4, n advantageously representing 2.

According to a preferred embodiment, the present invention relates to a monoethylenically unsaturated monomer M having the formula (I) below:

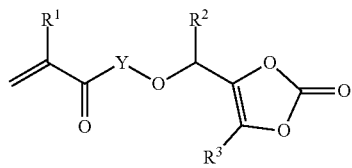

(I)

wherein:
$R^1$ represents a hydrogen atom or a methyl radical;
$R^2$ represents a hydrogen atom, a linear or branched alkyl radical comprising from 1 to 10 carbon atoms, a cycloalkyl radical comprising from 3 to 10 carbon atoms, an aryl (preferably phenyl) radical or an arylalkyl (preferably phenylalkyl) radical;
$R^3$ represents a hydrogen atom, a linear or branched alkyl radical comprising from 1 to 10 carbon atoms, a cycloalkyl radical comprising from 3 to 10 carbon atoms, an aryl (preferably phenyl) radical or an arylalkyl (preferably phenylalkyl) radical;
or $R^2$ and $R^3$ may be bonded together to form a $-(CH_2-)_p-$ group with p being an integer ranging from 3 to 5;
Y represents a bond or a $-X_1-(CH_2)_n-X_2-$ radical with:
  $X_1$ represents O, S, NH or NR' with R' representing an alkyl radical preferably comprising from 1 to 6 carbon atoms, $X_1$ preferably representing O;
  $X_2$ represents NHC(O) or C(O), $X_2$ preferably representing NHC(O);
  n represents an integer ranging from 2 to 10, preferably from 2 to 10, preferentially from 2 to 4, n advantageously representing 2.

Preferably, Y represents a bond or an $O-CH_2CH_2-NH-C(O)-$ radical.

According to one embodiment, the monomer M according to the invention is chosen from the monomers of formula (I-1) below:

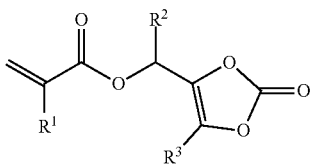

(I-1)

wherein $R^1$, $R^2$ and $R^3$ are as defined above. The monomers of formula (I-1) are those for which Y represents a bond.

According to one embodiment, the monomer M according to the invention is chosen from the monomers of formula (I-2) below:

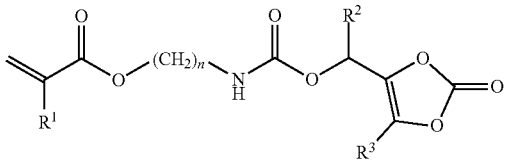

(I-2)

wherein $X_1$, $X_2$, n, $R^1$, $R^2$ and $R^3$ are as defined above. The monomers of formula (I-2) are those for which Y represents an $—X_1—(CH_2)_n—X_2—$ radical, in particular of $—O—(CH_2)_n—NH(CO)$-type.

Preferably, in the formulae (A), (A'), (I), (I-1) and (I-2):

$R^1$ represents a methyl radical or a hydrogen atom; and/or $R^2$ represents a hydrogen atom; and/or $R^3$ represents a linear or branched alkyl radical comprising from 1 to 10 carbon atoms, preferably $R^3$ represents a methyl radical.

The monomers M may be prepared by any conventional method known to those skilled in the art.

According to a preferred embodiment, the monomers M are chosen from one of the following monomers:

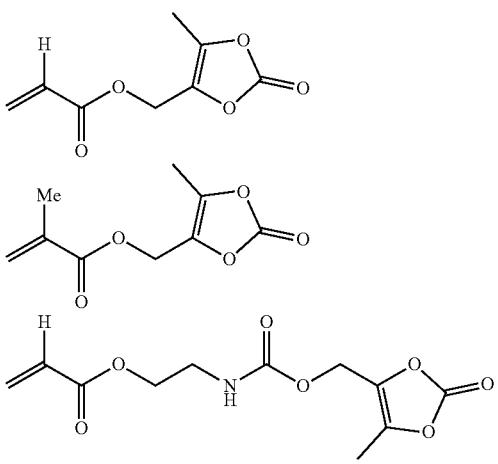

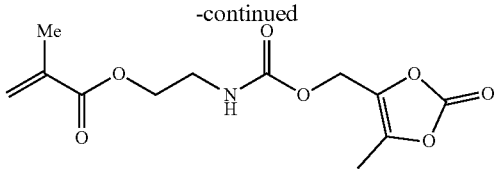

The present invention also relates to a process for preparing monomers M as defined above.

In particular, the present invention also relates to a process for preparing abovementioned monomers M, from a compound of formula (II) below:

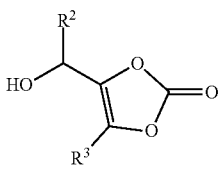

(II)

wherein $R^2$ and $R^3$ are as defined above.

According to one embodiment, the present invention relates to a process for preparing monomers M of formula (I-1) as defined above, comprising the reaction between a compound of formula (II):

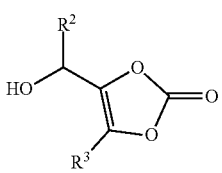

(II)

wherein $R^2$ and $R^3$ are as defined above; and a compound of formula (III):

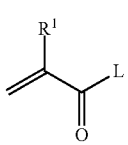

(III)

wherein $R^1$ is as defined above, and L represents a leaving group, for example a radical chosen from the group consisting of halogens, hydroxyl (OH) groups and alkoxy groups comprising from 1 to 10 carbon atoms, preferably from 1 to 8 carbon atoms, and advantageously from 1 to 4 carbon atoms.

The reaction between the compound of formula (II) and of formula (III) as defined above can be carried out under the conditions typical of nucleophilic substitution reactions, for example of an esterification or transesterification reaction.

According to one embodiment, the compounds of formula (III) are such that L represents a radical chosen from the group consisting of hydroxyl (OH) groups and alkoxy groups comprising from 1 to 10 carbon atoms, preferably from 1 to 8 carbon atoms, and advantageously from 1 to 4 carbon atoms. The reaction carried out corresponds in this case to an esterification or to a transesterification.

Among the compounds of formula (III), mention may for example be made of (meth)acrylic acid esters of C1 to C8 alcohols, such as methyl, ethyl, n-butyl and 2-ethylhexyl (meth)acrylates, and more particularly the (meth)acrylic acid esters of C1 to C4 alcohols, for example methyl, ethyl and n-butyl (meth)acrylates.

The abovementioned reaction between a compound of formula (II) and of formula (III) may be carried out in the presence of an acid catalyst (esterification reaction), a basic catalyst (transesterification reaction), or an enzymatic catalyst (esterification or transesterification reaction).

The enzyme-catalyzed esterification or transesterification may be carried out according to the methods described in Biotechnol. Lett. 1990, 12, 825-830, Biotechnol. Lett. 1994, 16, 241-246, and also applications U.S. Pat. No. 5,240,835, WO 2004/05088 or DE 102,009,003,035.

The enzymes (E) that can be used for the esterification or transesterification may be chosen from hydrolases, esterases (EC 3.1.-.-), lipases (EC 3.1.1.3), glycosylases (EC 3.2.-.-) and proteases (EC 3.4.-.-), in free form or in a form chemically or physically immobilized on a support, preferably lipases, esterases or proteases. Particular preference is given to Novozym® 435 from Novozymes (lipase from *Candida antarctica B*) or to the *Aspergillus* sp., *Aspergillus Niger* sp., *Mucor* sp., *Penicillium cyclopium* sp., *Geotricum candidum* sp., *Rhizopus javanicus, Burkholderia* sp., *Candida* sp., *Pseudomonas* sp. or porcine pancreas lipases, the *Candida antarctica B* and *Burkholderia* sp. lipases are very particularly preferred.

The enzyme content in the reaction medium may be within a range from 0.1% to 10% by weight relative to the total weight of the reactants of formulae (II) and (III) used.

The acid catalysts suitable for an esterification reaction are, for example, sulfuric acid, sodium hydrogen sulfate, hydrochloric acid, phosphoric acid, monosodium dihydrogen phosphate, disodium hydrogen phosphate, pyrophosphoric acid, phosphorous acid, hypophosphorous acid, methanesulfonic acid, trifluoromethanesulfonic acid, paratoluenesulfonic acid, and mixtures thereof. Lewis acids can also be used, such as, for example, compounds derived from titanium and from tin. It is also possible to use ion-exchange resins in their acid form, for example of sulfonic or carboxylic type.

The basic catalysts suitable for a transesterification reaction are, for example, metal hydroxides and/or alkoxides, in particular catalysts using metals from groups 1, 2, 4 and 13 of the periodic table, for example alkali metal hydroxides such as NaOH or KOH, and metal and alkaline-earth metal alkoxides, in particular the corresponding methoxides or ethoxides, such as sodium methoxide, potassium methoxide, sodium ethoxide or potassium ethoxide. Ion-exchange resins in their alkaline form can also be used.

The acid or basic catalysts can be used at concentrations ranging from 0.0001% to 20% by weight, preferably 0.001% to 10% by weight, relative to the total weight of the reaction mixture.

The reaction between the compound of formula (II) and the compound of formula (III) can be carried out continuously, batchwise, or semi-continuously.

In the case of a batch process, the compounds of formulae (II) and (III) can be added in a batch reactor, with addition of the catalyst or the enzyme.

In the case of a semi-continuous process, one of the reactants, for example the compound (II) or the compound (III), can be initially loaded and all or part of the other reactants can be introduced during the reaction.

In the case of a continuous process, the compounds (II) and (III) are introduced continuously to a reaction zone comprising the catalyst, the monomer M of formula (I) being continuously removed from the reaction zone, optionally with the co-products formed during the reaction, for example an alcohol or an ester.

The acid or basic or enzymatic catalysts can also be introduced continuously into the reaction zone in semi-continuous or continuous processes.

The reaction time depends in particular on factors such as the temperature, the amount of catalyst, the activity of the acid, basic or enzymatic catalyst used, the desired degree of conversion and/or the structure of the compounds of formula (II) and (III). The reaction time can be adjusted so that the conversion of the compound of formula (II) reaches at least 70%, preferably at least 80%, preferentially at least 90%, more preferentially still at least 95% and even more at least 97%. Generally, 1 to 48 hours, preferably 1 to 12 hours and more preferably 1 to 6 hours of reaction time may be sufficient to achieve the desired degree of conversion.

The esterification and transesterification reactions under acid or basic or enzymatic catalysis can generally be carried out at temperatures of between 0° C. and 100° C., preferably between 20° C. and 80° C. and more preferentially still between 20° C. and 70° C.

The molar ratio between the compound of formula (II) and the compound of formula (III) can vary over a wide range.

The molar ratio between the compound of formula (II) and the compound of formula (III) (compound of formula (II):compound of formula (III)) may be in the range from 1:100 to 1:1, preferably 1:50 to 1:1 and more preferably 1:20 to 1:1.

Preferably, the compound of formula (III) is used in excess relative to the compound of formula (II), so that it can be removed by distillation under reduced pressure, for example in the form of an azeotrope, at the same time as the co-product released, generally an alcohol or the co-product of the ester formed during a transesterification. It is also possible to shift the reaction equilibrium in favor of the monomer M of formula (I) by trapping the water or alcohol formed by means of a molecular sieve.

The reaction between the compound of formula (II) and the compound of formula (III) can be carried out in at least one organic solvent. Preferably, the reaction is carried out in the absence of organic solvent.

The organic solvent is preferably anhydrous, i.e. it contains a water content of less than 10% by volume, preferably less than 5% by volume, more preferably less than 1% by volume.

The proportion of organic solvents in the reaction mixture can vary from 0.1% to 50% by weight, preferably from 0.5% to 30% by weight or from 1% to 10% by weight, relative to the total weight of the reaction mixture.

The reaction can be carried out in the presence of at least one polymerization inhibitor. Among the polymerization inhibitors, mention may be made, for example, of 4-methoxyphenol (MEHQ), hydroquinone, 2,5-di-tert-butylhydroquinone, 2,6-di-tert-butyl-p-cresol (BHT), nitroso compounds, such as isoacryloyl nitrate, nitrosodiphenylamine, N-nitrosocyclohexylhydroxylamine, methylene blue, phenothiazine or diphenylamine, preferably the polymerization inhibitor is 4-methoxyphenol (MeHQ).

The polymerization inhibitors are generally used, on the basis of the amount of the compounds of formula (I), namely from 1 to 10000 ppm, preferably from 10 to 5000 ppm, more preferentially from 30 to 2500 ppm and in particular from 50 to 1500 ppm.

The compounds of formula (III) are typically known and available industrially.

According to one embodiment, the present invention relates to a process for preparing monomers M of formula (I-2) as defined above, comprising the reaction between a compound of formula (II):

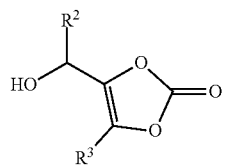

(II)

wherein $R^2$ and $R^3$ are as defined above;
and a compound having the general formula (IV) below:

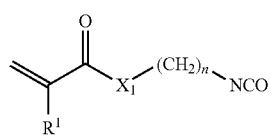

(IV)

wherein $R^1$, $X_1$ and n are as defined above.

Preferably, the compounds of formula (IV) are such that n is an integer ranging from 2 to 4, n preferentially representing 2.

Among the compounds of formula (IV), mention may for example be made of 2-isocyanatoethyl acrylate (CAS number: 13641-96-8) available from SHOWA DENKO EUROPE, or 2-isocyanatoethyl methacrylate (CAS number: 30674-80-7) available from SHOWA DENKO EUROPE.

Preferably, the compounds of formula (II) are those having one of the formulae (II-a) or (II-b) below:

compounds of formula (II-a):

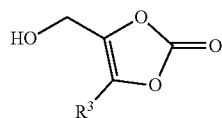

(II-a)

compounds of formula (II-b):

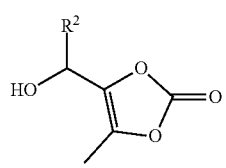

(II-b)

The abovementioned compounds of formula (II) may be prepared according to the procedure described in patent applications EP 0,078,413 and WO 9,602,253:

Scheme (1)

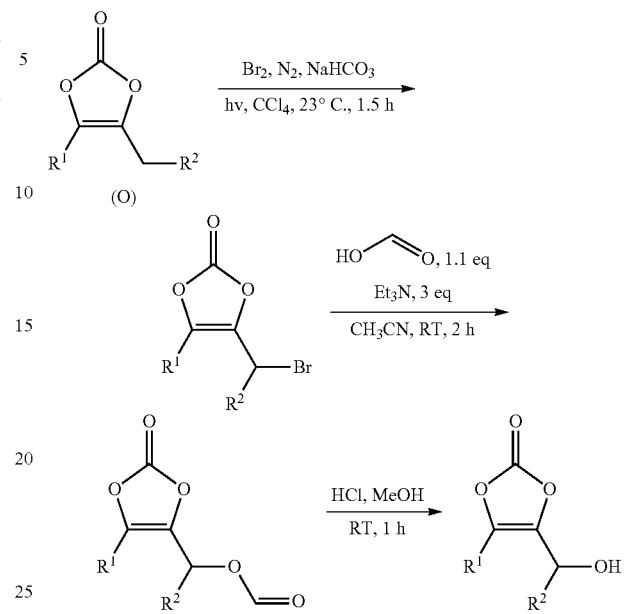

The starting compound (O) can be synthesized by the methods known to those skilled in the art described in Liebigs Annalen der Chemie, Vol. 764, pages 116-124 (1972), Tetrahedron Letters, 1972, pages 1701-1704 and U.S. Pat. No. 3,020,290 by JEFFERSON CHEMICAL.

The compound of formula (II-a) can be obtained according to scheme (2) below, by following the procedure described in WO 9,602,253:

Scheme (2)

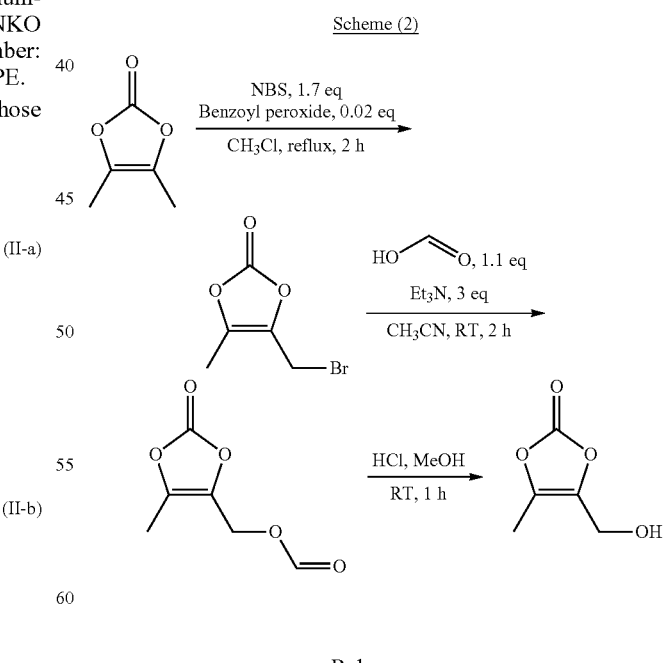

Polymers

The invention also relates to polymers comprising at least one repeating unit of general formula (V) below, preferably at least two repeating units:

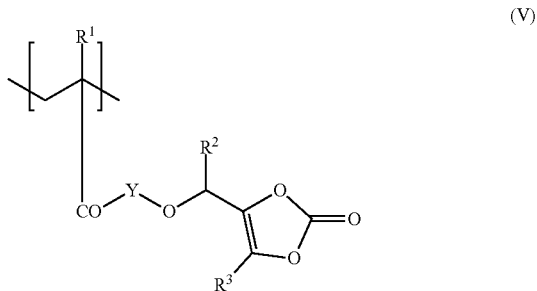

(V)

wherein Y, $R^1$, $R^2$ and $R^3$ are as defined above.

Preferably, the polymers according to the invention comprise from 1 to 1000 repeating units of abovementioned formula (V), preferably from 2 to 1000 repeating units of abovementioned formula (V).

Preferably, the repeating units of formula (V) are chosen from the repeating units of formula (V-a) or (V-b) below:

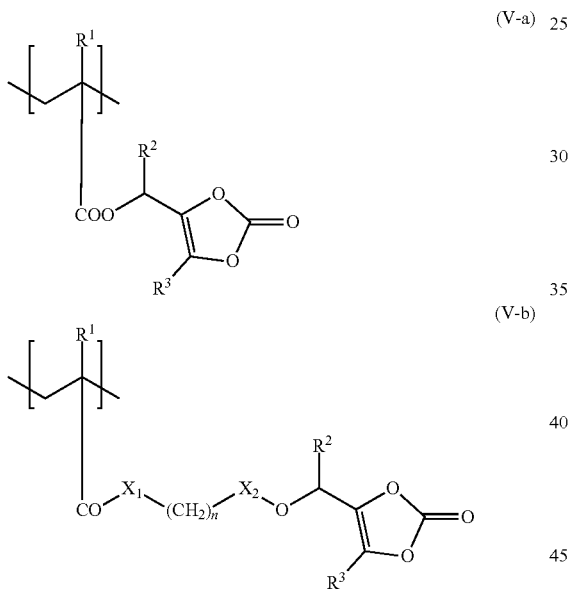

(V-a)

(V-b)

wherein n, $X_1$, $X_2$, $R^1$, $R^2$ and $R^3$ are as defined above.

Within the context of the invention, the term polymer covers both homopolymers and copolymers.

The polymers according to the invention can comprise at least 10% by weight of repeating units of formula (V), preferably at least 15% by weight, advantageously at least 20% by weight, more advantageously still at least 30% by weight relative to the total weight of repeating units present in the polymer.

The polymers according to the invention can comprise 100% by weight of repeating units of abovementioned formula (V).

According to one embodiment, the repeating units of the polymers according to the invention consist of the repeating units of abovementioned formula (V), advantageously resulting from the polymerization of a single monomer M as defined above, and in particular of formula (I). It is in this case a homopolymer.

Polymer Preparation Process

According to a preferred embodiment, the polymers according to the invention are obtained by polymerization of at least one abovementioned monomer M, in particular having the formula (I) as defined above, optionally in the presence of at least one ethylenically unsaturated monomer different from a monomer M.

The repeating units of abovementioned formula (V) are in particular derived from the monomers of abovementioned formula (I). When the polymers are obtained from at least one ethylenically unsaturated monomer different from a monomer M (in addition to at least one monomer M), said polymers comprise in particular repeating units derived from said ethylenically unsaturated monomers.

According to one embodiment, a polymer according to the invention is a homopolymer obtained by polymerization of a single monomer M, in particular of a single monomer of abovementioned formula (I).

According to one embodiment, a polymer according to the invention is a copolymer obtained:
  either by reaction between at least two different monomers M, optionally in the presence of at least one ethylenically unsaturated monomer different from a monomer M;
  or by reaction between at least one monomer M and at least one ethylenically unsaturated monomer different from a monomer M.

The present invention also relates to a process for preparing a polymer comprising a step of polymerizing at least one monomer M, optionally in the presence of at least one ethylenically unsaturated monomer different from a monomer M.

The ethylenically unsaturated monomers different from a monomer M may be monoethylenically unsaturated monomers (monomers B), and/or multiethylenically unsaturated monomers (monomers C).

The monomers B may be chosen from the following families:
  B1: Monoethylenically unsaturated C3 to C8 carboxylic acids and monoethylenically unsaturated C4 to C8 dicarboxylic acids such as, for example, acrylic acid, methacrylic acid, vinylacetic acid, crotonic acid, fumaric acid, maleic acid and itaconic acid;
  B2: Monoethylenically unsaturated C3 to C8 carboxylic acid amides and monoethylenically unsaturated C4 to C8 dicarboxylic acid diamides such as acrylamide, methacrylamide, N-methylolacrylamide, fumaramide and maleimide;
  B3: Monoethylenically unsaturated C4 to C8 acid anhydrides such as maleic anhydride;
  B4: Esters of monoethylenically unsaturated C3 to C8 carboxylic acids and C2 to C4 alcohols such as 2-hydroxyethyl acrylate, 2-hydroxypropyl acrylate, 3-hydroxypropyl acrylate, 2-hydroxybutyl acrylate, 4-hydroxybutyl acrylate, 2-hydroxyethyl methacrylate, 2-hydroxypropyl methacrylate, 3-hydroxypropyl methacrylate, 2-hydroxybutyl methacrylate, 4-hydroxybutyl methacrylate and equivalents thereof based on monoethylenically unsaturated C4 to C8 dicarboxylic acids;
  B5: Monoethylenically unsaturated sulfonic acids (and also the alkali metal or ammonium salts thereof), for example vinylsulfonic acid, allylsulfonic acid, methallylsulfonic acid, vinylbenzenesulfonic acid, 2-acrylamido-2-methylpropanesulfonic acid, 2-methacrylamido-2-methylpropane acid, 2-acrylamidoethanesulfonic acid, 2-methacryloyloxyethanesulfonic acid, acrylam idoethanesulfonic acid, 2-acryloyloxyethanesulfonic acid, 3-acryloyloxypropanesulfonic acid and 2-methacryloyloxypropanesulfonic acid;

B6: Monoethylenically unsaturated C3 to C5 nitriles, such as acrylonitrile and methacrylonitrile;

B7: Heterocyclic N-vinyl derivatives such as N-vinylpyrrolidone, N-vinylcaprolactam and N-vinylimidazole;

B8: Monoethylenically unsaturated compounds comprising a C2 (EO), C3 (PO) and C4 (BO) poly(alkylene oxide) group, for example vinyl and allyl ethers of alkoxylated C1 to C10 polyalkylene glycols, glycols or alcohols, and also the corresponding esters of monoethylenically unsaturated C3 to C8 carboxylic acids and monoethylenically unsaturated dicarboxylic acids with glycols and C2 (EO), C3 (PO) and C4 (BO) poly (alkylene glycol)s derived from C1 to C14 alcohols.

B9: Vinyl aromatic derivatives such as styrene, α-methylstyrene and vinyltoluene isomers;

B10: Esters of monoethylenically unsaturated C3 to C8 carboxylic acids and of C1 to C20 alcohols, of C5 to C8 cyclic alcohols, of C1 to C4 alcohols comprising a phenyl group or of C1 to C4 alcohols comprising a phenoxy group, for example esters of acrylic acid with C1 to C20 alcohols such as methyl acrylate, ethyl acrylate, n-butyl acrylate, 2-butyl acrylate, isobutyl acrylate, tert-butyl acrylate, 2-ethylhexyl acrylate, decyl acrylate, lauryl acrylate, stearyl acrylate, esters of acrylic acid with C5 to C10 cycloalkanols, such as cyclohexyl acrylate, esters of acrylic acid with C1 to C4 alcohols comprising a phenyl group, such as benzyl acrylate, 2-phenylethyl acrylate and 1-phenylethyl acrylate, esters of acrylic acid with C1 to C4 alcohols comprising a phenoxy group, for example 2-phenoxyethyl acrylate, esters of a methacrylic acid with C1 to C20 alcohols, preferably C1 to C10 alcohols, such as methyl methacrylate, ethyl methacrylate, n-butyl methacrylate, 2-butyl methacrylate, isobutyl methacrylate, tert-butyl methacrylate, 2-ethylhexyl methacrylate, decyl methacrylate, lauryl methacrylate and stearyl methacrylate, esters of methacrylic acid with C5 to C10 cycloalkanols such as cyclohexyl methacrylate or isobornyl methacrylate, esters of methacrylic acid with C1 to C4 alcohols comprising a phenyl group, such as benzyl methacrylate, 2-phenylethyl methacrylate and 1-phenylethyl methacrylate, and also esters of methacrylic acid with C1 to C4 alcohols comprising a phenoxy group, such as 2-phenoxyethyl methacrylate;

B11: Diesters of monoethylenically unsaturated C4 to C8 acids and of C1 to C20 alcohols, of C5 to C8 cycloalkanols, of C1 to C4 alcohols comprising a phenyl group or of C1 to C4 alcohols comprising a phenoxy group;

B12: Alkylamides and dialkylamides of monoethylenically unsaturated C3 to C8 carboxylic acids and of C1 to C20 primary or secondary amines, in particular alkylamides and dialkylamides of acrylic acid and methacrylic acid, for example ethylacrylamide, dimethylacrylamide, diethylacrylamide, n-propylacrylamide, N-butylacrylamide, laurylacrylamide, stearylacrylamide, ethylmethacrylamide, dimethylmethacrylamide, diethylmethacrylamide, n-propylmethacrylamide, N-butylmethacrylamide, laurylmethacrylamide, steaylmethacrylamide;

B13: Vinyl esters of C1 to C20 atom aliphatic carboxylic acids, for example vinyl acetate, vinyl propionate, vinyl butyrate, vinyl hexanoate, vinyl laurate, vinyl stearate and vinyl versatate;

B14: Conjugated and unsaturated C4 to C10 olefins such as butadiene and isoprene;

B15: C2 to C20 olefins such as ethylene, propene, 1-butene, 2-butene, isobutene, 1-hexene, 1-octene, diisobutene and 1-decene;

B16: C2 to C20 olefins substituted with a halogen atom such as vinyl chloride, vinylidene chloride, vinyl bromide, fluoroethene, 1,1-difluoroethene and tetrafluoroethene;

B17: Monoethylenically unsaturated monomers having one or two epoxy groups, such as monoesters and diesters of C3 to C8 monounsaturated ethylenic acids and C3-C10 epoxy alcohols, for example glycidyl monoesters of monoethylenically unsaturated C3 to C8 acids or glycidyl diesters of monoethylenically unsaturated C4 to C8 dicarboxylic acids such as glycidyl acrylate and glycidyl methacrylate, or monoethylenically unsaturated ethers based on C3 to C10 epoxy alcohols, in particular allyl and methallyl ethers, for example allyl glycidyl ether and methallyl glycidyl ether;

B18: Monoethylenically unsaturated monomers comprising at least one carbonate group, in particular a cyclic carbonate group, for example a 1,3-dioxolan-2-one group or a 4-methyl-1,3-dioxolan-2-one group, for example propylene carbonate acrylate, (1,3-dioxolan-2-one-4-yl)methyl acrylate (glycerol carbonate acrylate) or (1,3-dioxolan-2-one-4-yl) methyl methacrylate (glycerol carbonate methacrylate);

B19: Esters of monoethylenically unsaturated C3 to C8 carboxylic acids or monoethylenically unsaturated C4 to C8 dicarboxylic acids with C8 to C24 unsaturated alcohols or C8 to C24 unsaturated diols, in particular esters of acrylic acid or methacrylic acid, for example oleyl acrylate, oleyl methacrylate, linoleyl acrylate or methacrylate and linolenyl acrylate or methacrylate.

B20: Esters of monoethylenically unsaturated C3 to C8 carboxylic acids or of monoethylenically unsaturated C4 to C8 dicarboxylic acids bearing an alkoxysilane group chosen from trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl methacrylate, triethoxysilylpropyl methacrylate, tributoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, trimethoxysilylpropyl acrylate, triethoxysilylpropyl acrylate, or tributoxysilylpropyl acrylate.

B21: Monoethylenically unsaturated monomers comprising phosphonates chosen from N-methacrylamidomethylphosphonic acid ester derivatives, in particular the n-propyl ester (RN 31857-11-1), the methyl ester (RN 31857-12-2), the ethyl ester (RN 31857-13-3), the n-butyl ester (RN 31857-14-4), the isopropyl ester (RN 51239-00-0), and also the phosphonic monoacid and diacid derivatives thereof, such as N-methacrylamidomethylphosphonic diacid (RN 109421-20-7);

N-methacrylamidoethylphosphonic acid ester derivatives, such as N-methacrylamidoethylphosphonic acid dimethyl ester (RN 266356-40-5), N-methacrylamidoethylphosphonic acid di(2-butyl-3,3-dimethyl) ester (RN 266356-45-0), and also the phosphonic monoacid and diacid derivatives thereof, such as N-methacrylamidoethylphosphonic diacid (RN 80730-17-2); N-acrylamidomethylphosphonic acid ester derivatives such as N-acrylamidomethylphosphonic acid dimethyl ester (RN 24610-95-5), N-acrylamidomethylphosphonic acid diethyl ester (RN 24610-96-6), bis(2-chloropropyl) N-acrylamidomethyl phosphonate (RN 50283-36-8), and also the phosphonic monoacid and diacid derivatives thereof, such as N-acrylamidomethyl phosphonic acid (RN 151752-38-4); vinylbenzylphosphonate dialkyl ester derivatives, in particular the di(n-propyl) (RN 60181-26-2), di(isopropyl) (RN 159358-34-6), diethyl (RN 726-61-4), dimethyl (RN 266356-24-5), di(2-butyl-3,3-dimethyl) (RN 266356-29-0) and di(t-butyl) (RN 159358-33-5) ester derivatives, and also the phosphonic monoacid and diacid variants thereof, such as vinylbenzylphosphonic diacid (RN 53459-43-1); diethyl 2-(4-vinylphenyl)ethanephosphonate (RN 61737-88-0); dialkylphosphonoalkyl acrylates and methacrylates, such as 2-(acryloyloxy)ethylphosphonic acid dimethyl ester (RN 54731-78-1) and 2-(methacryloyloxy)ethylphosphonic acid dimethyl ester (RN 22432-83-3), 2-(methacryloyloxy)methylphosphonic acid diethyl ester (RN 60161-88-8), 2-(methacryloyloxy)methylphosphonic acid dimethyl ester (RN 63411-25-6), 2-(methacryloyloxy)propylphosphonic acid dimethyl ester (RN 252210-28-9), 2-(acryloyloxy)methylphosphonic acid diisopropyl ester (RN 51238-98-3), 2-(acryloyloxy)ethylphosphonic acid diethyl ester (RN 20903-86-0), and also the phosphonic monoacid and diacid variants thereof, such as 2-(methacryloyloxy)ethylphosphonic acid (RN 80730-17-2), 2-(methacryloyloxy)methylphosphonic acid (RN 87243-97-8), 2-(methacryloyloxy)propylphosphonic acid (RN 252210-30-3), 2-(acryloyloxy) propylphosphonic acid (RN 254103-47-4) and 2-(acryloyloxy)ethylphosphonic acid; vinylphosphonic acid, optionally substituted by cyano, phenyl, ester or acetate groups, vinylidenephosphonic acid, in the form of sodium salt or the isopropyl ester thereof, bis(2-chloroethyl) vinylphosphonate, it being possible for these monomers having a phosphonic monoacid or diacid function to be used in the partially or completely neutralized form, optionally neutralized by an amine, for example dicyclohexylamine, B22: monoethylenically unsaturated monomers chosen from the phosphate analogs of the phosphonate monomers described above, the monomers then comprising a —C—O—P—sequence in comparison with the —C—P-sequence of the phosphonates;

B23: monoethylenically unsaturated monomers comprising at least one boronate function or a precursor chosen, for example, from acryloylbenzeneboronic acid, methacryloylbenzeneboronic acid, 4-vinylbenzeneboronic acid, 3-acrylamidophenylboronic acid, 3-methacrylamidophenylboronic acid, alone or as mixtures, or in the form of salts;

B24: amides of vinylamine, in particular vinylformamide, vinylacetamide, N-vinylpyrrolidone and N-vinylcaprolactam;

B25: monoethylenically unsaturated monomers comprising a tertiary amino group, or a heterocyclic group containing nitrogen such as for example vinylpyridines, vinylimidazole, aminoalkyl (meth)acrylates and aminoalkyl (meth)acrylamides such as dimethylaminoethyl acrylate, dimethylaminoethyl methacrylate, di-tert-butylaminoethyl acrylate, di-tert-butylaminoethyl methacrylate, dimethylaminomethyl acrylamide, dimethylaminomethyl methacrylamide, dimethylaminopropyl acrylamide, dimethylaminopropyl acrylamide or zwitterionic monomers such as, for example, sulfopropyl(dimethyl)aminopropyl acrylate.

The preferred monomers B are the monomers from groups B1, B2, B4, B5, B6, B8, B9, B10, B12 and B13, in particular the monomers from groups B9, such as preferably vinyl aromatics in particular styrene, and B10, preferably esters of acrylic acid or methacrylic acid with C1 to C20 alcohols, and combinations of monomers B1, B2, B4, B5, B6, B8, B9, B10, B12 and B13, in particular B9 and/or B10, with one or more monomers from group B17, B18 or B19.

The monomers C may be chosen from diesters and triesters of carboxylic acids having C=C unsaturations, in particular bisacrylates and triacrylates of diols or polyols having 3 or more OH groups, for example bis(acrylates) and bis(methacrylates) of ethylene glycol, diethylene glycol, triethylene glycol, neopentyl glycol or polyethylene glycol.

Such monomers C are advantageously used in an amount ranging from 0.01% to 10% by weight, relative to the total weight of monomers introduced.

The nature of the ethylenically unsaturated monomers that can be used, and also the amounts thereof, may vary depending on the particular end application for which the polymer is intended.

According to a preferred embodiment, the polymer according to the invention is a copolymer comprising:
- at least one repeating unit, preferably at least two repeating units of abovementioned general formula (V); and
- at least one repeating unit resulting from the polymerization of at least one monomer B chosen from monomers B9, B10 and mixtures thereof, preferably from styrene, butyl acrylate, methyl methacrylate, isobornyl methacrylate, and mixtures thereof.

Preferably, the polymer according to the invention is a copolymer comprising:
- at least 10% by weight, preferably from 15% to 80% by weight of repeating units of abovementioned general formula (V) relative to the total weight of the repeating units;
- at least 10% by weight, preferably from 10% to 60% by weight, preferentially from 15% to 50% by weight of repeating units resulting from the polymerization of at least one monomer B chosen from monomers B9, preferably styrene, relative to the total weight of repeating units;
- from 1% to 50% by weight of repeating units resulting from the polymerization of at least one B10 monomer, preferably chosen from butyl acrylate, methyl methacrylate, isobornyl methacrylate, and mixtures thereof.

The polymers according to the invention may have a number-average molecular mass (Mn) ranging from 1000 to 1000000 dalton, preferably ranging from 1200 to 100000 dalton.

The polymers according to the invention may have a weight-average molecular mass (Mw) ranging from 1200 to 5000000 dalton, preferably ranging from 2000 to 2000000 dalton.

The number-average (Mn) or weight-average (Mw) molar masses indicated for the polymers are determined by gel permeation chromatography in THF (or GPC, also known as size exclusion chromatography or SEC), with calibration relative to a certified external molecular weight polystyrene standard.

According to one embodiment, the process for preparing a polymer according to the invention comprises a step of polymerizing:
- at least one monomer M, preferably of formula (I), and
- at least one monoethylenically unsaturated monomer B preferably chosen from monomers B9, B10 and mixtures thereof.

Preferably, the polymerization step is carried out under the following conditions:
- the total content of monomer(s) M, preferably of monomer(s) of formula (I), is greater than or equal to 10% by weight, preferably greater than or equal to 20% by weight, advantageously greater than or equal to 30% by weight, and more preferentially greater than or equal to 35% by weight, relative to the total weight of monomers introduced; and/or
- the total content of monomer(s) B9 is greater than or equal to 10% by weight, preferably greater than or equal to 15% by weight, and advantageously greater than or equal to 20% by weight, relative to the total weight of monomers introduced; and/or
- the total content of monomer(s) B10 is greater than or equal to 5% by weight, preferably greater than or equal to 10% by weight, advantageously greater than or equal to 15% by weight, and more advantageously still greater than or equal to 20% by weight, for example greater than or equal to 30% by weight, relative to the total weight of monomers introduced.

The polymerization step according to the invention can be carried out by conventional radical polymerization processes such as solution polymerization, precipitation polymerization, suspension polymerization, emulsion polymerization or mini-emulsion polymerization.

In one embodiment, the polymerization step is carried out in a non-aqueous solvent or in a non-aqueous diluent as a polymerization medium, it being possible for said solvent or diluent to comprise small amounts of water, if necessary. On the basis of the total volume of the reaction mixture, the amount of water may usually be less than 2% by weight, in particular less than 1% by weight and more preferentially less than 0.5% by weight. As a general rule, the amount of water, on the basis of the monomer, may be at most 10% by weight, usually less than or equal to 5% by weight, in particular less than or equal to 2% by weight and in particular less than or equal to 1% by weight.

Suitable solvents or diluents are in particular those in which the monomers to be polymerized are soluble. It is also possible to polymerize in organic solvents in which the monomers to be polymerized are insoluble. The polymerization is then advantageously carried out in the form of an oil-in-oil emulsion or of a suspension polymerization, in which case, depending on the ratios of monomers and of organic solvent, the monomers form the continuous phase or preferably the dispersed phase.

The polymerization step can be carried out in at least one solvent chosen from aprotic solvents, protic solvents and mixtures thereof.

Among the aprotic solvents, mention may for example be made of aliphatic and cycloaliphatic hydrocarbons, such as n-hexane, n-heptane, cyclohexane, halogenated hydrocarbons such as dichloromethane, 1,2-dichloroethane, aromatic hydrocarbons and halogenated aromatic hydrocarbons such as benzene, toluene, xylenes, chlorobenzene, dichlorobenzenes, anhydrides of aliphatic carboxylic acids, carboxylic acids or carboxylic acid derivatives that are non-polymerizable such as acetic anhydride, esters of C1 to C4 aliphatic monocarboxylic acids and C1 to C6 linear alcohols or C5 to C6 cyclic alcohols, such as methyl acetate, ethyl acetate, propyl acetate, n-butyl acetate, methyl butyrate, ethyl butyrate, propyl butyrate, methyl propionate, ethyl propionate, ethyl 3-ethoxypropionate, propyl propionate, ethyl formate, butyl formate, cyclohexyl acetate and the like, esters of monoalkyl ether alcohol and C1 to C4 aliphatic monocarboxylic acids, such as 1-methoxy-2-propyl acetate or 2-methoxyethyl acetate, N,N-dialkylamides of C1 to C4 aliphatic monocarboxylic acids such as N,N-dimethylformamide (DMF), N,N-dimethylacetamide, N—(C1 to C4)alkyl lactams such as N-methylpyrrolidone (NMP), N-ethylpyrrolidone, C1 to C4 dialkyl sulfoxides such as dimethyl sulfoxide (DMSO), C3 to C8 cyclic and acyclic ketones, such as methyl ethyl ketone, acetone and cyclohexanone, C1 to C4 aliphatic dialkyl ethers, cycloaliphatic ethers and aromatic ethers such as diethyl ether, tert-butyl methyl ether, dioxane, tetrahydrofuran, monoglyme and anisole, and both cyclic and acyclic saturated carbonates having preferably 3 to 8 carbon atoms, such as ethylene carbonate (1,3-dioxolan-2-one) and propylene carbonate, dialkyl carbonates of C1 to C4 alcohols such as dimethyl carbonate, diethyl carbonate, dipropyl carbonate, dibutyl carbonate, and mixtures thereof.

Among the protic solvents, mention may in particular be made of aliphatic alcohols, such as C2 to C4 alkylene glycols, monoalkyl ethers of C1 to C4 diols, such as 1-methoxy-2-propanol and 1-methoxy-2-methyl-2-propanol, propanol, C1 to C4 monoalkyl ethers of C2-C4 glycols, C1 to C10 alcohols such as methanol, ethanol, n-propanol, isopropanol, n-butanol, 2-butanol, isobutanol, tert-butanol, amyl alcohol, isoamyl alcohol, and mixtures thereof.

The preferred solvents are esters of C1 to C4 aliphatic monocarboxylic acids and C1 to C6 alcohols such as n-butyl acetate, ethyl 3-ethoxypropionate, C2 to C4 alkylene glycols, C1 to C4 monoalkyl ethers of C2 to C4 diols such as 1-methoxy-2-methyl-2-propanol and 1-methoxy-2-propanol, dialkyl carbonates of C1-C4 dialkyl alcohols such as dimethyl carbonate, diethyl carbonate, dipropyl carbonate, dibutyl carbonate, cyclic carbonates such as ethylene carbonate and propylene carbonate, ethers such as glymes and anisole.

Preferably, the solvent is ethyl 3-ethoxypropionate.

In the case of precipitation polymerization, the solvent or diluent is an organic solvent or a diluent in which the copolymer is insoluble.

In the case of solution polymerization, the solvent is an organic solvent in which the copolymer is soluble.

The organic solvent is such that the amount of monomers to be polymerized, relative to the total amount of monomers and solvent, advantageously ranges from 10% to 65% by weight, in particular from 20% to 60% by weight.

Free radicals are generally formed using what is referred to as a polymerization initiator, namely a compound which forms free radicals by decomposition, which can be initiated chemically, thermally or photochemically.

The polymerization according to the invention is advantageously carried out in the presence of at least one polymerization initiator.

The polymerization initiators are advantageously chosen from the group consisting of organic azo compounds, hydroperoxides, organic peroxides, inorganic peroxides, redox initiators, and mixtures thereof.

The organic peroxides are in particular selected from tert-butyl peroxyacetate, tert-butyl peroxyisobutyrate, tert-butyl peroxybenzoate, tert-butyl peroxy-2-ethylhexanoate, tert-butyl peroxypivalate, tert-butyl peroxyneodecanoate, tert-amyl peroxypivalate, acetyl peroxide, benzoyl peroxide, lauroyl peroxide, caproyl peroxide and cumyl peroxide.

The hydroperoxides are in particular chosen from hydrogen peroxide, organic hydroperoxides such as cumene hydroperoxide, tert-butyl hydroperoxide, tert-amyl hydroperoxide and the like.

The azo compounds are in particular chosen from 2,2'-azobisisobutyronitrile (AIBN), 2,2'-azobis(2-methylbutyronitrile), 1,1'-azobis(1-cyclohexanecarbonitrile), 2,2'-azobis(2,4-dimethylvaleronitrile), 4,4'-azobis(4-pentanoic acid), 2-(t-butylazo)-2-cyanopropane, 2,2'-azobis[2-methyl-N-(1,1)-bis(hydroxymethyl)-2-hydroxyethyl]propionamide, 2,2'-azobis(2-methyl-N-[1,1-bis(hydroxymethyl)-2-hydroxyethyl]propionamide), 2,2'-azobis(2-m ethyl-N-[1,1-bis(hydroxymethyl)ethyl]propionamide), 2,2'-azobis(N,N'-dimethyleneisobutyram idine), 2,2'-azobis(2-methylpropionamidine), N-(3-hydroxy-1,1-bis(hydroxymethyl)propyl)-2-[1-(3-hydroxy-1,1-bis(hydroxymethyl)propylcarbamoyl)-1-methylethylazo]-2-methylpropionamide and N-(1-ethyl-3-hydroxypropyl)-2-[1-(1-ethyl-3-hydroxypropylcarbamoyl)-1-methylethylazo]-2-methylpropionamide.

The inorganic peroxides are in particular chosen from peroxydisulfuric acid and salts thereof, such as ammonium peroxodisulfate, sodium peroxodisulfate and potassium peroxodisulfate.

Redox initiators are understood to mean initiator systems which comprise an oxidizing agent, for example a peroxodisulfuric acid salt, hydrogen peroxide, or an organic peroxide such as tert-butyl hydroperoxide and a reducing agent.

The reducing agents are in particular a sulfur compound, preferably chosen from sodium hydrogen sulfite, sodium hydroxymethanesulfinate or the addition product of hydrogen sulfite on acetone. Other suitable reducing agents are phosphorus compounds such as phosphorous acid, hypophosphites and phosphinates and hydrazine or hydrazine hydrate and ascorbic acid. Moreover, redox initiator systems may include addition of small amounts of redox metal salts, such as iron salts, vanadium salts, copper salts, chromium salts or manganese salts, for example ascorbic acid/iron (II), sodium sulfate/peroxodisulfate as the redox initiator system.

Particularly preferred initiators for the polymerization process according to the invention are azo compounds, in particular azobisisobutyronitrile (AIBN).

For the radical polymerization of the monomers, these polymerization initiators are generally used in an amount of from 0.01% to 5% by weight, in particular in an amount of from 0.1% to 3% by weight, relative to the total weight of the monomers to be polymerized.

The polymerization initiator can be initially loaded into the polymerization reactor or added during the polymerization reaction. The procedure will usually be to add at least some of the initiator, preferably at least 50% by weight and preferably at least 80% by weight of the polymerization initiator, during the polymerization reaction.

It is also preferable to load some of the monomers at the start of the reaction, for example 0.1% to 20% by weight, relative to the total amount of monomers to be polymerized, optionally with all or some of the polymerization initiator and all or some of the solvent or diluent into the polymerization vessel, to start the polymerization, for example by heating the polymerization mixture, then by adding the rest of the monomers and, where appropriate, the rest of the polymerization initiator and a solvent during the polymerization.

The polymerization temperatures typically used for the polymerization are, depending on the initiator system chosen, generally in the range from 20° C. to 180° C., in particular in the range from 40° C. to 130° C. and in particular in the range from 50° C. to 120° C.

The polymerization may be carried out under a slightly reduced pressure, for example above 800 mbar, under normal pressure of normal pressure or under high pressure, for example up to 10 bar, although higher or lower pressures may also be used.

The polymerization time generally does not exceed 10 hours, this polymerization being advantageously carried out in 1 to 8 hours.

The polymerization process according to the invention may be carried out in standard reactors used for a radical polymerization, for example stirred batch reactors with stirred tanks in cascade, or tubular reactors, which reactors may optionally be equipped with static and/or dynamic mixers. The reactors are generally equipped with one or more devices for introducing the reactants, devices for withdrawing the products, equipment for supplying and controlling the heat of reaction, control means for controlling and/or monitoring the parameters of the reaction (pressure, temperature, conversion, etc.). The reactors can be operated in batch mode or continuously.

Once the polymerization is complete, the reaction mixture can be treated in the usual manner. In the case of a precipitation polymerization, the polymer may for example be separated by filtration. The volatile components, for example solvents, can be removed by distillation. In the case of a solution polymerization, it is also possible to precipitate the polymer obtained, for example by adding an organic solvent in which the polymer is insoluble. The polymerization may also be followed by a solvent exchange, for example to change from a solution to a dispersion. Optionally, the polymer obtained may be subjected to devolatilization, in order to eliminate other volatile constituents (VOCs).

The monoethylenically unsaturated monomers according to the invention advantageously result in polymers comprising functions of formula (A) having improved reactivities at crosslinking temperatures below 60° C., preferably below or equal to 35° C., and more preferably still at room temperature (23° C.), especially in the presence of primary and secondary polyamines.

The present invention also relates to a solution comprising at least one organic solvent and at least one polymer as described above.

The organic solvent may be chosen from aprotic solvents, protic solvents and mixtures thereof.

Among the aprotic solvents, mention may for example be made of aliphatic and cycloaliphatic hydrocarbons, such as n-hexane, n-heptane, cyclohexane, halogenated hydrocarbons such as dichloromethane, 1,2-dichloroethane, aromatic hydrocarbons and halogenated aromatic hydrocarbons such as benzene, toluene, xylenes, chlorobenzene, dichlorobenzenes, anhydrides of aliphatic carboxylic acids, carboxylic acids or carboxylic acid derivatives that are non-polymerizable such as acetic anhydride, esters of C1 to C4 aliphatic monocarboxylic acids and C1 to C6 linear alcohols or C5 to C6 cyclic alcohols, such as methyl acetate, ethyl acetate, propyl acetate, n-butyl acetate, methyl butyrate, ethyl butyrate, propyl butyrate, methyl propionate, ethyl propionate, ethyl 3-ethoxypropionate, propyl propionate, ethyl formate, butyl formate, cyclohexyl acetate and the like, esters of monoalkyl ether alcohol and C1 to C4 aliphatic monocarboxylic acids, such as 1-methoxy-2-propyl acetate or 2-methoxyethyl acetate, N,N-dialkylamides of C1 to C4 aliphatic monocarboxylic acids such as N,N-dimethylformamide (DMF), N,N-dimethylacetamide, N—(C1 to C4)alkyl lactams such as N-methylpyrrolidone (NMP), N-ethylpyrrolidone, C1 to C4 dialkyl sulfoxides such as dimethyl sulfoxide (DMSO), C3 to C8 cyclic and acyclic ketones, such as methyl ethyl ketone, acetone and cyclohexanone, C1 to C4 aliphatic dialkyl ethers, cycloaliphatic ethers and aromatic ethers such as diethyl ether, tert-butyl methyl ether, dioxane, tetrahydrofuran, monoglyme and anisole, and both cyclic and acyclic saturated carbonates having preferably 3 to 8 carbon atoms, such as ethylene carbonate (1,3-dioxolan-2-one) and propylene carbonate, dialkyl carbonates of C1 to C4 alcohols such as dimethyl carbonate, diethyl carbonate, dipropyl carbonate, dibutyl carbonate, and mixtures thereof.

Preferably, the organic solvent is ethyl 3-ethoxypropionate. The abovementioned solution preferably comprises more than 50% by weight of polymer (solids content) as defined above, preferably 55% by weight, and advantageously more than 60% by weight, relative to the total weight of said solution.

Compositions

The present invention also relates to a composition comprising:
  a composition A comprising at least one polymer as defined above; and
  a composition B comprising at least one compound C comprising at least two functional groups F, which are identical or different, for example from 2 to 10 functional groups F, chosen from aliphatic hydroxyls, aliphatic primary or secondary amines, aliphatic mercaptans, aliphatic phosphines, and phosphonates.

It may be the polymer comprising at least one repeating unit of formula (V) mentioned above, or a polymer obtained by polymerization of at least one abovementioned monomer M optionally in the presence of at least one ethylenically unsaturated monomer different from a monomer M.

The polymer may optionally be in solid form or in solution in the solvent used for the polymerization step.

Preferably, the composition comprises:
  a composition A comprising at least one polymer as defined above; and
  a composition B comprising at least one compound C comprising at least two functional groups F, which are identical or different, for example from 2 to 10 functional groups F, chosen from aliphatic hydroxyls, aliphatic primary or secondary amines and aliphatic mercaptans, said functional groups F preferably being chosen from aliphatic hydroxyls and aliphatic primary or secondary amines.

According to one embodiment, the amount of compound(s) C is chosen so that the molar ratio of functions of abovementioned formula (A):functional groups F of the compound(s) C is between 1:10 and 10:1, preferentially between 5:1 and 1:5 and more preferentially between 1:2 and 2:1.

Compound C may be a low molecular mass compound, which means that its molar mass is less than or equal to 500 g/mol, or an oligomer/polymer having a number-average molecular mass (Mn) of greater than 500 g/mol.

Compound C is preferably chosen from amino compounds, alcoholic compounds, amino acids (for example lysine, arginine, glutamine and asparagine, and stereoisomers thereof), and mixtures thereof, and preferentially chosen from amino compounds, alcoholic compounds and mixtures thereof.

The amino compounds include in particular aliphatic polyamines, cycloaliphatic polyamines, aromatic polyamines, arylaliphatic polyamines, polymeric amines, polyamidoamines, polyetheramines, and mixtures thereof.

Among the aliphatic polyamines, mention may for example be made of ethylenediamine, 1,2-propanediamine, 1,3-propanediamine, neopentanediamine, hexamethylenediamine, octamethylenediamine, 1,10-diaminodecane, 1,12-diaminododecane, diethylenetriamine, triethylenetetramine, tetraethylenepentamine, polyethyleneimines (PEIs), polyethyleneimine dendrimers, polypropyleneimines (PPIs), polypropyleneimine dendrimers, poly(propylene-ethylene) imines, tris(aminoethyl)amine (TAEA), tris(aminopropyl) amine (TAPA), 2,2-dimethylpropylenediamine, trimethylhexamethylenediamine, 1-(3-aminopropyl)-3-aminopropane, 1,3-bis(3-aminopropyl)propane, 4-ethyl-4-methylamino-1-octylamine and mixtures thereof.

Among the polymeric amines, mention may for example be made of poly(vinylamine)s and poly(allylamine)s.

Among the cycloaliphatic polyamines, mention may for example be made of 1,2-diaminocyclohexane, 1,2-bis(aminomethyl)cyclohexane, 1,3-bis(aminomethyl)cyclohexane, 1,4-bis(aminomethyl)cyclohexane, 1-methyl-2,4-diaminocyclohexane, N-cyclohexylpropylene-1,3-diamine, 4-(2-aminopropan-2-yl)-1-methylcyclohexane-1-amine, isophoronediamine, 4,4'-diaminodicyclohexylmethane (Dicykan), 3,3'-dimethyl-4,4'-diaminodicyclohexylmethane, 3,3',5,5'-tetramethyl-4,4'-diaminodicyclohexylmethane, 4,8-diaminotricyclo[5.2.1.0]decane, norbornane diamine, menthane diamine, menthene diamine and mixtures thereof.

Among the arylaliphatic polyamines, mention may for example be made of xylylenediamines and, in particular, meta-xylylenediamine (MXDA).

Among the cyclic polyamines, mention may for example be made of piperazine, N-aminoethylpiperazine, and mixtures thereof.

Among the polyetheramines, mention may for example be made of:
  difunctional and trifunctional primary polyetheramines based on polypropylene glycol, polyethylene glycol, polybutylene glycol, poly (1,4-butanediol), polytetrahydrofuran (polyTHF) or polypentylene glycol, for example 4,7,10-trioxamidecane-1,3-diamine, 4,7,10-trioxamidecane-1,13-diamine, 1,8-diamino-3,6-dioxaoctane (for example XTJ-504 sold by HUNTSMAN), 1,10-diamino-4,7-dioxadecane (for example XTJ-590 sold by HUNTSMAN), 1,12-diamino-4,9-dioxadodecane (for example sold by BASF SE), 1,3-diamino-4,7,10-trioxamidecane (for example marketed by BASF SE),
  difunctional primary polyetheramines based on polypropylene glycol, for example polyetheramine D 230 (sold by BASF SE) or Jeffamine D 230 (sold by HUNTSMAN) having an average molar mass of 230 g/mol,
  difunctional primary polyetheramines based on polypropylene glycol, for example polyetheramine D 400 (sold by BASF SE) or Jeffamine® XTJ 582 (sold by HUNTSMAN) having an average molecular mass of 400 g/mol, polyetheramine D 2000 (sold by BASF SE), Jeffamine D2000 or Jeffamine® XTJ 578 (sold by HUNTSMAN) having an average molar mass of 2000 g/mol and polyetheramine D 4000 (sold by BASF SE) having an average molar mass of 4000 g/mol, trifunctional primary polyetheramines prepared by reaction of propylene oxide with trimethylolpropane followed by amination of the terminal OH groups, for example polyetheramine T 403 (sold by BASF SE) or Jeffamine® T 403 (sold by HUNTSMAN) with an average molar mass of 403 g/mol, trifunctional primary polyetheramines prepared by reaction of propylene oxide with glycerol followed by amination of the terminal OH groups, for example polyetheramine T 5000 (sold by BASF SE) or Jeffamine® T 5000 (sold by HUNTSMAN) with an average molar mass of 5000 g/mol, difunctional primary polyetheramines formed by reaction of propylene oxide with polyethylene glycol followed by amination of the terminal OH groups, for example Jeffamine® ED-600 or Jeffamine® XTJ 501 (sold by HUNTSMAN) having an average molar mass of 600 g/mol, Jeffamine® ED-900 (sold by HUNTSMAN) having an average molar mass of 900 g/mol, Jeffamine® ED-2003 (sold by HUNTSMAN) having an average molar mass of 2000 g/mol, Jeffamine® HK-511 (sold by HUNTSMAN) having an average molar mass of 220 g/mol, difunctional primary polyetheramines based on a copolymer of poly(tetramethylene ether glycol) and polypropylene glycol, for example Jeffamine® XTJ-542 (sold by HUNTSMAN) having an average molecular mass of 1000 g/mol, Jeffamine XTJ-548 (sold by HUNTSMAN) having an average molecular mass of 1900 g/mol, Jeffamine XTJ-559 (sold by HUNTSMAN) having an average molecular mass of 1400 g/mol, trifunctional polyetheramines prepared by reaction of butylene oxide with a triol followed by amination of the terminal OH groups, for example Jeffamine XTJ-566 (sold by HUNTSMAN) having an average molar mass of 400 g/mol and Jeffamine XTJ-568 (sold by HUNTSMAN) having an average molar mass of 219 g/mol, tetrafunctional primary polyetheramines prepared by reaction of propylene oxide with pentaerythritol, for example Jeffamine XTJ-616 (sold by HUNTSMAN) having an average molecular mass of 600 g/mol, difunctional primary polyetheramines based on triethylene glycol, for example Jeffamine EDR-148 (sold by HUNTSMAN) having an average molecular mass of 148 g/mol, difunctional primary polyetheramines prepared by amination of glycols, for example Jeffamine EDR-176 (HUNTSMAN) having an average molar mass of 176 g/mol, and also difunctional primary polyetheramines prepared by amination of polytetrahydrofuran (polyTHF), for example PolyTHF®-amine 350 (sold by BASF SE) having an average molar mass of 250 g/mol; and mixtures thereof.

The polyamidoamines (amidopolyamines) may be those obtained by reaction of dimeric fatty acids (for example dimeric linoleic acid) with low molecular weight polyamines, such as diethylenetriamine, 1-(3-aminopropyl)-3-aminopropane, triethylenetetramine or other diamines, such as the aforementioned aliphatic or cycloaliphatic diamines.

The amino compounds are preferentially chosen from aliphatic polyamines, in particular 2,2-dimethylpropylenediamine, aromatic diamines, in particular m-xylylenediamine (MXDA), cycloaliphatic diamines, in particular isophoronediamine, N-cyclohexylpropylene-1,3-diamine and 4,4'-diaminodicyclohexylmethane (Dicykan), difunctional or trifunctional primary polyetheramines based on polypropylene glycol, for example, Jeffamine D 230 or Jeffamine® T403, and mixtures thereof.

The alcoholic compounds are preferably chosen from:
aliphatic and cycloaliphatic alcohols having a molar mass of less than or equal to 250 g/mol, in particular chosen from 1,4-butanediol, ethylene glycol, diethylene glycol, triethylene glycol, neopentyl glycol, 1,3-propanediol, 1,5-pentanediol, 1,6-hexanediol, glycerol, diglycerol, pentaerythritol, dipentaerythritol, sorbitol, mannitol, and mixtures thereof;

polyols chosen from the group consisting of polyester polyols, polycarbonate polyols, polyether polyols, hydroxylated polyolefins, polyacrylate polyols, polyvinyl alcohols, and mixtures thereof;

and mixtures thereof.

The polyols chosen from the group consisting of polyester polyols, polycarbonate polyols, polyether polyols, polyacrylate polyols, polyvinyl alcohols, and mixtures thereof, preferably have a number average molecular mass (Mn) ranging from 250 to 50000 g/mol, preferably ranging from 500 to 10000 g/mol.

The number-average molar masses indicated for the polyols are determined by gel permeation chromatography in THF (or GPC, also known as size exclusion chromatography or SEC), with calibration relative to a certified external molecular weight polystyrene standard.

In general, polyester polyols are linear or branched compounds having ester groups in the polymer backbone and having free hydroxyl groups at the ends of the polymer chain. Typically, these may be polyesters which are obtained by polycondensation of diols and dicarboxylic acids, optionally in the presence of higher polyalcohols (for example tri-, tetra-, penta- or hexavalent alcohols) and/or higher polyfunctional carboxylic acids. Rather than di- or polycarboxylic acids, it is also possible to use esters of di- or polycarboxylic acids or anhydrides of the corresponding di- or polycarboxylic acids or mixtures thereof for the preparation of the polyester polyols. The di- or polycarboxylic acids may be aliphatic, cycloaliphatic, aryl aliphatic, aromatic or heterocyclic, saturated or unsaturated, generally having from 2 to 50 carbons and in particular from 4 to 20 carbon atoms that are optionally substituted, for example by halogen atoms. The carboxylic acids are chosen, for example, from suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, alkenylsuccinic acid, fumaric acid and dimeric fatty acids.

The diols used for the preparation of the polyester polyols may comprise aliphatic and cycloaliphatic diols generally having from 2 to 40 carbons and in particular, from 2 to 20 carbon atoms, for example ethylene glycol, propane-1,2-diol, propane-1,3-diol, butane-1,3-diol, butane-1,4-diol, butene-1,4-diol, butyne-1,4-diol, pentane-1,5-diol, neopentyl glycol, bis(hydroxymethyl)cyclohexane such as 1,4-bis(hydroxymethyl)cyclohexane, 2-methylpropane-1,3-diol, methylpentanediol, and also diethylene glycol, triethylene glycol, tetraethylene glycol, polyethylene glycol, dipropylene glycol, polypropylene glycol, dibutylene glycol and polybutylenes. Alcohols of the general formula below are preferred:

HO—(CH$_2$)$_x$—OH wherein x is a number ranging from 2 to 20, preferably an even number ranging from 2 to 12. As examples, mention may be made of ethylene glycol, butane-1,4-diol, hexane-1,6-diol, octane-1,8-diol and dodecane-1,12-diol. The preferred alcohols are neopentyl glycol and pentane-1,5-diol.

The alcoholic compounds which can be used may also be chosen from lactone-based polyester polyols, these being homopolymers or copolymers of lactones, preferably the addition products of lactones on suitable difunctional starting molecules. Useful lactones are in particular those derived from compounds of the general formula below:

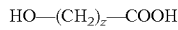

wherein z is a number ranging from 1 to 20 and a hydrogen atom of a methylene unit may also be substituted by a C1-C4 alkyl radical. Examples are ε-caprolactone, β-propiolactone, γ-butyrolactone and/or methyl-ε-caprolactone and mixtures thereof. Suitable starting molecules are, for example, low molecular weight dialcohols mentioned above as a formation component for the polyester polyols. The corresponding polymers of ε-caprolactone are particularly preferred. It is also possible to use lower polyester diols or polyether diols as "starters" for the preparation of the lactone polymers. Rather than the polymers of lactones, it is also possible to use the corresponding chemically equivalent polycondensates of the hydroxycarboxylic acids corresponding to the lactones.

Examples of polyester polyols are cited, for example, in Ullmann's Encyclopedia of Industrial Chemistry, 4th edition, volume 19, pages 62 to 65.

Among the polycarbonate polyols, mention may for example be made of those obtained by reaction of phosgene with an excess of low molecular weight alcohols.

Among the polyether polyols, mention may for example be made of those prepared by polymerization of ethylene oxide, propylene oxide, butylene oxide, tetrahydrofuran, styrene oxide or epichlorohydrin, for example in the presence of $BF_3$, successively or as a mixture, onto bi- or polyfunctional starting components having reactive hydrogen atoms, such as polyols or polyfunctional amines, for example water, ethylene glycol, propane-1,2-diol, propane-1,3-diol, 1,1-bis(4-hydroxyphenyl)propane, trimethylolpropane, glycerol, sorbitol, ethanolamine or ethylenediamine. Use can also be made of polysaccharide polyethers, in particular those described in DE 1,176,358 and DE 1,064,938.

Among the hydroxylated polyolefins, mention may be made of those having at least 2 hydroxyl groups can be used, for example α,ω-dihydroxypolybutadiene (diPBOH).

Among the polyacrylate polyols, mention may for example be made of those in which the hydroxyl groups may be present in the middle and/or at the ends of the main chain. Mention will for example be made of α,ω-dihydroxypoly(meth)acrylates that may be obtained by homo-or copolymerization of esters of acrylic acid and/or of methacrylic acid, in the presence of regulators comprising OH groups, such as mercaptoethanol or alkyl mercaptopropanol, followed by a transesterification with a low molecular weight polyol, for example an alkylene glycol such as butanediol. Such polymers are described, for example, in patent application EP 0,622,378. Mention will also be made of the polymers that can be obtained by copolymerization of acrylates and/or methacrylates with hydroxyalkyl esters of unsaturated ethylenic carboxylic acids such as 2-hydroxyethyl acrylate, 2-hydroxypropyl acrylate, 2-hydroxybutyl acrylate, 2-hydroxyethyl methacrylate, 2-hydroxypropyl methacrylate or 2-hydroxybutyl methacrylate.

Among the polyvinyl alcohols, which are generally obtained by partial or complete hydrolysis of vinyl esters, mention may in particular be made of polyvinyl acetate. If it is a partially hydrolyzed polyvinyl acetate, the degree of hydrolysis of the acetates does not exceed 50% to 95%. If it is a completely hydrolyzed polyvinyl acetate, the degree of hydrolysis of the acetates ranges from 95% to 100%.

The total amount of compound(s) C in the composition may range from 0.1% to 50% by weight, often from 0.5% to 40% by weight, preferably from 1% to 30% by weight, relative to to the total weight of the ingredients in the composition.

Preferably, the composition comprises:
a composition A comprising at least one polymer as defined above; and
a composition B comprising at least one compound C chosen from amino compounds, and in particular ethylenediamine.

Preferably, the composition comprises:
from 50% to 98% by weight of a composition A comprising at least one polymer as defined above; and
from 2% to 50% of a composition B comprising at least one compound C chosen from amino compounds, and in particular ethylenediamine,
the percentages by weight being percentages by weight relative to the total weight of the composition.

The composition according to the invention may comprise at least one additive chosen from the group consisting of catalysts, fillers, antioxidants, light stabilizers/UV absorbers, metal deactivators, antistatic agents, antifogging agents, foaming agents, biocides, plasticizers, lubricants, emulsifiers, colorants, pigments, rheological agents, impact modifiers, adhesion promoters, optical brighteners, flame retardants, antidripping agents, nucleating agents, solvents, reactive diluents and mixtures thereof.

Preferably, the composition according to the invention comprises at least one solvent.

These additives may be present in composition A and/or composition B of the composition according to the invention, and/or in an additional component (different from composition A and from composition B).

The fillers customarily used are, for example, inorganic or organic powders, for example calcium carbonates and silicates, and inorganic fibrous materials, for example glass fibers. It is also possible to use organic fillers such as carbon fibers, and mixtures of organic and inorganic fillers, for example mixtures of glass fibers and carbon fibers, or mixtures of carbon fibers and inorganic fillers. The fillers can be added in an amount ranging from 1% to 75% by weight, based on the total weight of the composition.

The UV stabilizers, the antioxidants and also the metal deactivators used in the compositions according to the invention advantageously have a good resistance to migration and a high thermal stability. They are chosen, for example, from the following groups a) to t). the compounds of groups a) to g) and i) are light stabilizers/UV absorbers, whereas the compounds j) to t) act as stabilizers:
a) 4,4-diarylbutadienes,
b) cinnamic esters,
c) benzotriazoles,
d) hydroxybenzophenones,
e) diphenyl cyanacrylates,
f) oxamides,
g) 2-phenyl-1,3,5-triazines,
h) antioxidants,
i) nickel compounds,
j) sterically hindered amines,
k) metal deactivators,
l) phosphites and phosphonites, m) hydroxylamines,
n) nitrones,
o) amine oxides,
p) benzofuranones and indolinones,
q) thiosynergists,
r) peroxide destroyers,
s) polyamide stabilizers and
t) basic costabilizers.

The catalysts are optionally used in proportions ranging from 0.01% to around 10% by weight, relative to the total weight of the polymer(s) of the invention having repeating units of formula (V) and of compound(s) C.

According to one embodiment, when the compound C comprises amines as functional groups F, the use of catalyst is optional, which means that the catalyst content in the composition is advantageously less than 0.01% by weight.

The catalysts are preferably used when the compound C has reactive groups other than amines as functional groups F, in particular when they are hydroxyl groups.

The catalysts used are preferentially basic catalysts, in particular organic amines and organic phosphines. Among the organic amines, preference is given to amidines, for example 1,8-diazabicyclo[5.4.0]undec-7-ene (DBU) and 1,5-diazabicyclo[4.3.0]non-5-ene (DBN) and C1 to C6 mono-, di- and trialkylamines, in particular triethylamine and tert-butylamine. Among the organic phosphines, trialkylphosphines and triarylphosphines, for example tri-n-butylphosphine and triphenylphosphine, are preferred. The catalyst may also be used in the form of mixtures, optionally in combination with tri(C1 to C6)alkylammonium halides and copper salts, for example triphenylphosphine, in combination with a tri(C1 to C6)alkylammonium halide and a copper salt, for example copper (I) chloride, copper (II) bromide, copper (II) chloride or copper (II) sulfate.

The choice of additives used is advantageously a function of the final use which is made of the composition according to the invention, which can be adjusted according to the application specifications by those skilled in the art.

The solvents may be organic solvents, for example chosen from aprotic solvents, protic solvents and mixtures thereof.

Among the aprotic solvents, mention may for example be made of aliphatic and cycloaliphatic hydrocarbons, such as n-hexane, n-heptane, cyclohexane, halogenated hydrocarbons such as dichloromethane, 1,2-dichloroethane, aromatic hydrocarbons and halogenated aromatic hydrocarbons such as benzene, toluene, xylenes, chlorobenzene, dichlorobenzenes, anhydrides of aliphatic carboxylic acids, carboxylic acids or carboxylic acid derivatives that are non-polymerizable such as acetic anhydride, esters of C1 to C4 aliphatic monocarboxylic acids and C1 to C6 linear alcohols or C5 to C6 cyclic alcohols, such as methyl acetate, ethyl acetate, propyl acetate, n-butyl acetate, methyl butyrate, ethyl butyrate, propyl butyrate, methyl propionate, ethyl propionate, ethyl 3-ethoxypropionate, propyl propionate, ethyl formate, butyl formate, cyclohexyl acetate and the like, esters of monoalkyl ether alcohol and C1 to C4 aliphatic monocarboxylic acids, such as 1-methoxy-2-propyl acetate or 2-methoxyethyl acetate, N,N-dialkylamides of C1 to C4 aliphatic monocarboxylic acids such as N,N-dimethylformamide (DMF), N,N-dimethylacetamide, N—(C1 to C4)alkyl lactams such as N-methylpyrrolidone (NMP), N-ethylpyrrolidone, C1 to C4 dialkyl sulfoxides such as dimethyl sulfoxide (DMSO), C3 to C8 cyclic and acyclic ketones, such as methyl ethyl ketone, acetone and cyclohexanone, C1 to C4 aliphatic dialkyl ethers, cycloaliphatic ethers and aromatic ethers such as diethyl ether, tert-butyl methyl ether, dioxane, tetrahydrofuran, monoglyme and anisole, and both cyclic and acyclic saturated carbonates having preferably 3 to 8 carbon atoms, such as ethylene carbonate (1,3-dioxolan-2-one) and propylene carbonate, dialkyl carbonates of C1 to C4 alcohols such as dimethyl carbonate, diethyl carbonate, dipropyl carbonate, dibutyl carbonate, and mixtures thereof.

Preferably, the solvent is butyl acetate.

According to one embodiment, the composition according to the invention comprises:
a composition A comprising:
at least one polymer as defined above, preferably in a mass content greater than or equal to 30% by weight, preferably greater than or equal to 40% by weight, advantageously greater than or equal to 50% by weight relative to the total weight of said composition A;
at least one organic solvent,
a composition B comprising at least one compound C comprising at least two functional groups F, which are identical or different, for example from 2 to 10 functional groups F, chosen from aliphatic hydroxyls, aliphatic primary or secondary amines and aliphatic mercaptans, said functional groups F preferably being chosen from aliphatic hydroxyls and aliphatic primary or secondary amines;
optionally a composition D comprising at least one organic solvent, such as for example butyl acetate.

The organic solvent of composition A can be the organic solvent used for the preparation of the polymer (polymerization step). It can therefore be one of the aprotic or protic solvents mentioned above, and preferably 3-ethoxypropionate.

The presence of an organic solvent in the composition according to the invention can advantageously make it possible to adapt the viscosity of the composition in view of the use thereof.

Uses of the Composition

The compositions according to the invention can be thermally crosslinked by heating the mixture of compositions A and B at a temperature above the mixing temperature or at lower temperatures.

Preferably, the compositions according to the invention are crosslinked at temperatures between 0° C. and 200° C., preferably between 10° C. and 150° C., preferably between 23° C. and 80° C. and in particular between 23° C. and 40° C.

The crosslinking can also be induced using microwaves.

The present invention also relates to the use of the composition according to the invention for the production of coatings, paint or adhesives, or else for the production of 3D objects.

The compositions according to the invention can be applied for the purpose of producing a coat of paint by all the customary application processes, for example spraying, knife coating, painting, casting, dip coating or roll coating.

Use is preferably made of spray application methods, for example compressed air spraying, airless spraying, high-speed rotation, electrostatic spray application (ESTA), optionally combined with hot spraying, for example hot air spraying. The application can be carried out at temperatures between from 70° C. to 80° C. maximum, so that the appropriate viscosity of the composition is attained. For example, the hot spraying may be configured so that the coating composition is heated only very briefly in the spray nozzle, or slightly upstream thereof.

The spray booth used for the application may be equipped with a temperature-controllable circulating system, which can optionally be used with an absorption medium suitable for the spraying, for example the coating composition itself.

The application of the compositions according to the invention may also be carried out in such a way that the components are mixed only a short time before the application, namely in a mixing chamber upstream of the spray nozzle, this application method being particularly suitable for compositions having very short pot lives.

The application processes described above may also be used for the production of other coats of paint or lacquer during the production of a multicoat system. In this case, it is possible to use different coating materials for each of the different coats. Preference is given to application on a base coat.

Possible substrates include all paintable surfaces that lend themselves to combined curing, either primed or unprimed, such as for example metals, plastics, wood, ceramic, stone, textile, fiber composites, leather, glass, glass fibers, glass wool and rock wool, construction materials such as plaster boards, cement slabs, or tiles.

The compositions according to the invention are very particularly suitable for the formulation of structural adhesives in particular intended for the permanent joining of different materials or substrates such as plastics, metals, wood, leather, ceramic, etc. In a nonlimiting manner, the compositions according to the invention may for example be used for the laying and adhesive bonding of floor coverings, for the production of electronic circuits and all other forms of assembly requiring a multicomponent reactive system.

All the embodiments described above can be combined with one another. In particular, the various abovementioned constituents of the composition, and notably the preferred embodiments of the composition, may be combined with each other.

In the context of the invention, the term "of between x and y" or "ranging from x to y" is understood to mean an interval in which the limits x and y are included. For example, the range "between 0% and 25%" notably includes the values 0% and 25%.

The invention is now described in the following implementation examples, which are given purely by way of illustration and should not be interpreted in order to limit the scope thereof.

Experimental Section

A. Synthesis of the Polymerizable (meth)acrylic Monomers

Example 1

Preparation of 4,5-dimethyl-1,3-dioxolen-2-one (114.10 g/mol, CAS Number: 37830-90-3)

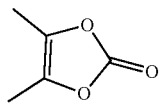

Triphosgene (60 g) is added to a solution of 3-hydroxy-2-butanone (44 g) in dichloroethane (500 mL) cooled on an ice bath (approx. 0° C.). N,N-dimethylaniline (72.7 g) diluted beforehand with an equal volume of dichloroethane is added dropwise to the reaction medium while maintaining the temperature below 8° C. After addition of N,N-dimethylaniline, the reaction mixture is left stirring for 15 minutes on an ice bath. The ice bath is removed, the reaction medium is left to return to room temperature and is kept stirring for 2 hours. The reaction mixture is cooled to 5° C. and washed with 3N hydrochloric acid cooled on ice, iced water and brine. The dichloroethane solution is dried over sodium sulfate, concentrated to around 250 mL, brought to reflux for 3 hours, then the solvent is removed under reduced pressure to obtain 67.92 g of residue. The crude product is heated at 170° C. under an inert atmosphere (under argon) for 2 hours. The resulting crude product is dissolved in toluene and decolorized over activated charcoal. The charcoal is removed by filtration and the filtrate is concentrated to around 100 mL. Hexane is added to 100 mL of solution and the mixture is placed on an ice bath for 20 minutes. The crystals formed are filtered off, washed with hexane at 0° C. and recrystallized from hexane. 41.86 g of a colorless solid are obtained (70% yield). Melting point: 80-81° C.

$^1$H NMR (CDCl$_3$, 400 MHz, 298 K) δ (ppm): 2.28 (2 s, 6H, O—C(O)—O—C(CH$_3$)=C—CH$_3$);

$^{13}$C NMR (CDCl$_3$, 100 MHz, 298 K) δ (ppm): 8.9 (O—C(O)—O—C(CH$_3$)=C—CH$_3$), 162.1 (O—C(O)—O—C(CH$_3$)=CCH$_3$), 153.1 (O—C(O)—O—C(CH$_3$)=C—CH$_3$).

Example 2

Preparation of 4-bromomethyl-5-methyl-1,3-dioxolen-2-one (193.0 g/mol, CAS Number: 80715-22-6)

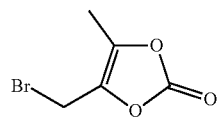

Variant A:

4,5-Dimethyl-1,3-dioxolen-2-one (11.4 g) from example 1 is mixed with N-bromosuccinimide (19.6 g) and benzoyl peroxide (0.7 g) in freshly distilled carbon tetrachloride (350 mL) and brought to reflux for 6 hours under an inert atmosphere (argon). The reaction mixture is then cooled on an ice bath and the precipitate formed is removed by filtration. The filtrate is washed with water and with brine, dried over sodium sulfate and extracted with dichloromethane, the solvent is removed under reduced pressure. A crude yellow oil (20.54 g) is obtained which is then distilled to obtain the pure 4-bromomethyl-5-methyl-1,3-dioxolen-2-one compound in the form of a light yellow oil (yield 90%); boiling point 93° C. at 0.45 mm;

$^1$H NMR (CDCl$_3$, 400 MHz, 298 K) δ (ppm): 2.31 (s, 3H, O—C(O)—O—C(CH$_3$)=C—CH$_2$—Br), 4.07 (s, 2H, O—C(O)—O—C(CH$_3$)=C—CH$_2$—Br);

$^{13}$C NMR (100 MHz, CDCl$_3$, 293 K) δ (ppm): 10.5 (O—C(O)—O—C(CH$_3$)=C—CH$_2$—Br), 25.9 (O—C(O)—O—C(CH$_3$)=C—CH$_2$—Br), 155.7 (O—C(O)—O—C(CH$_3$)=C—CH$_2$Br), 144.3 (O—C(O)—O—C(CH$_3$)=C—CH$_2$—Br), 153.0 (O—C(O)—O—C(CH$_3$)=C—CH$_2$—Br).

Variant B:

4-Chloromethyl-5-methyl-1,3-dioxolen-2-one (140 g, CHINOIN Pharmaceutical and Chemical Works) and sodium bromide (190 g) are mixed in dimethylformamide (300 mL) and kept stirring for 1 hour at room temperature. The reaction medium is filtered and washed with acetone. The filtrate is concentrated under reduced pressure. A crude yellow oil (20.54 g) is obtained which is then distilled to obtain the pure 4-bromomethyl-5-methyl-1,3-dioxolen-2-one compound in the form of a light yellow oil (yield 75%); boiling point 93° C. at 0.45 mm;

$^1$H NMR (CDCl$_3$, 400 MHz, 298 K) δ (ppm): 2.31 (s, 3H, O—C(O)—O—C(CH$_3$)=C—CH$_2$—Br), 4.07 (s, 2H, OC—(O)—O—C(CH$_3$)=C—CH$_2$—Br);

$^{13}$C NMR (100 MHz, CDCl$_3$, 293 K) δ (ppm): 10.5 (O—C(O)—O—C(CH$_3$)=C—CH$_2$—Br), 25.9 (O—C(O)—O—C(CH$_3$)=C—CH$_2$—Br), 155.7 (O—C(O)—OC(CH$_3$)=C—CH$_2$—Br), 144.3 (O—C(O)—O—C(CH$_3$)=C—CH$_2$Br), 153.0 (O—C(O)—O—C(CH$_3$)=C—CH$_2$—Br).

Example 3

Preparation of 4-formyloxymethyl-5-methyl-1,3-dioxolen-2-one (158.11 g/mol, CAS number: 91526-17-9)

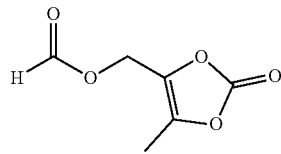

4-Bromomethyl-5-methyl-1,3-dioxolen-2-one (11.8 g) from example 2 is dissolved in a solution of trimethylamine (36 g), formic acid (11.4 g) and acetonitrile (250 mL), and then kept stirring for 1 hour at room temperature. The acetonitrile is evaporated off under reduced pressure, the residue is dissolved in water and extracted with ethyl acetate. The organic phase is washed with water and brine, dried over sodium sulfate and concentrated under reduced pressure. A light brown liquid is obtained (82% yield).

$^1$H NMR (CDCl$_3$, 400 MHz, 298 K) δ (ppm): 2.30 (s, 3H, O—C(O)—O—C(CH$_3$)=C—CH$_2$—O—CH=O), 4.79 (s, 2H, O—C(O)—O—C(CH$_3$)=C—CH$_2$—O—CH=O), 9.50 (s, 1 H, O—C(O)—O—C(CH$_3$)=C—CH$_2$—O—CH=O);

$^{13}$C NMR (100 MHz, CDCl$_3$, 293 K) δ (ppm): 10.5 (O—C(O)—O—C(CH$_3$)=C—CH$_2$—O—CH=O), 62.8 (O—C(O)—O—C(CH$_3$)=C—CH$_2$—O—CH=O), 144.3 (O—C(O)—O—C(CH$_3$)=C—CH$_2$—O—CH=O), 155.7 (O—C(O)—O—C(CH$_3$)=C—CH$_2$—O—CH=O), 153.0 (O—C(O)—O—C(CH$_3$)=C—CH$_2$—O—CH=O), 161.1 (O—C(O)—O—C(CH$_3$)=C—CH$_2$—O—CH=O).

Example 4

Preparation of 4-hydroxymethyl-5-methyl-1,3-dioxolen-2-one (130.10 g/mol, CAS Number: 91526-18-0)

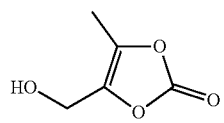

4-Formyloxymethyl-5-methyl-1,3-dioxolen-2-one (7.6 g) from example 3 is dissolved in methanol (100 mL) and 0.3 mL of 36% hydrochloric acid is added. The mixture is kept stirring for one hour at room temperature and the methanol is removed under reduced pressure. The residue is fixed on a silica gel column (100 g) and eluted with ethyl acetate. Pure 4-hydroxymethyl-5-methyl-1,3-dioxolen-2-one (93% yield) is obtained in the form of a colorless oil.

$^1$H NMR (CDCl$_3$, 400 MHz, 298 K) δ (ppm): 2.30 (s, 3H, O—C(O)—O—C(CH$_3$)=C—CH$_2$—OH), 4.03 (s, 2H, O—C(O)—O—C(CH$_3$)=C—CH$_2$—OH);

$^{13}$C NMR (100 MHz, CDCl$_3$, 293 K) δ (ppm): 10.5 (O—C(O)—O—C(CH$_3$)=C—CH$_2$—OH), 57.2 (O—C(O)—O—C(CH$_3$)=C—CH$_2$—OH), 144.3 (O—C(O)—O—C(CH$_3$)=C—CH$_2$—OH), 153 (O—C(O)—O—C(CH$_3$)=C—CH$_2$—OH), 155.7 (O—C(O)—O—C(CH$_3$)=C—OH$_2$—OH).

Example 5

Preparation of (5-methyl-1,3-dioxolen-2-one-4-yl) methyl acrylate (184.16 g/mol)

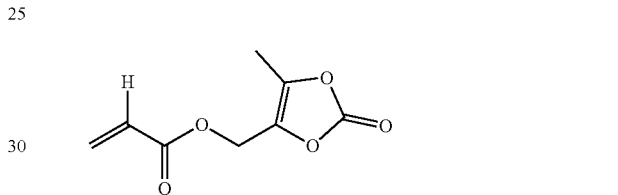

130 g of 4-hydroxymethyl-5-methyl-1,3-dioxolen-2-one (1.00 mol) from example 4, and 202.4 g of triethylamine (2.00 mol) are dissolved in 500 mL of dichloromethane. The reactor is placed under a light flow of nitrogen and cooled to −40° C. and then 100 g of acryloyl chloride (1.11 mol) are introduced slowly over a period of 1 hour. Once the addition is complete, the reaction medium is left to return to temperature, and kept stirring and under a flow of nitrogen for 2 hours at room temperature. The HCl generated is trapped in a bubbler containing a 4% sodium hydroxide solution. Once the reaction is complete, the reaction medium is neutralized and washed with 150 mL of a 10% sodium bicarbonate solution. The organic phase is separated, dried over sodium sulfate and concentrated at 40° C. under reduced pressure. (5-Methyl-1,3-dioxolen-2-one-4-yl) methyl acrylate is obtained in the form of a yellow oil with a purity of greater than 92% (74% yield).

$^1$H NMR (400 MHz, CDCl$_3$, 298 K) δ (ppm): 2.31 (s, 3H, O—C(O)—O—C(CH$_3$)=C—CH$_2$—O—C(O)—CH=CHH), 4.72 (s, 2H, O—C(O)—O—C(CH$_3$)=C—CH$_2$—O—C(O)—CH=CHH), 6.02 (dd, 1 H, O—C(O)—O—C(CH$_3$)=C—CH$_2$—O—C(O)—CH=CHH), 6.33 (dd, 1H, O—C(O)—O—C(CH$_3$)=C—CH$_2$—O—C(O)—CH=CHH), 6.87 (dd, 1H, O—C(O)—O—C(CH$_3$)=C—CH$_2$—O—C(O)—CH=CHH);

$^{13}$C NMR (100 MHz, CDCl$_3$, 298 K) δ (ppm): 10.5 (O—C(O)—O—C(CH$_3$)=C—CH$_2$—O—C(O)—CH=CHH), 62.8 (O—C(O)—O—C(CH$_3$)=C—CH$_2$—O—C(O)—CH=CHH), 128.0 (O—C(O)—O—C(CH$_3$)=C—CH$_2$—O—C(O)—CH=CHH), 131.1 (O—C(O)—O—C(CH$_3$)=C—CH$_2$—O—C(O)—CH=CHH), 155.7 (O—C(O)—O—C(CH$_3$)=C—CH$_2$—O—C(O)—CH=CHH), 144.3 (O—C(O)—O—C(CH$_3$)=C—CH$_2$—O—C(O)—CH=CHH), 153.0 (O—C(O)—O—C(CH$_3$)

=C—CH₂—O—C(O)—CH=CHH), 165.8 (O—C(O)—O—C(CH₃)=C—CH₂—O—C(O)—CH=CHH).

Example 6

Preparation of (5-methyl-1,3-dioxolen-2-one-4-yl) methyl methacrylate (DIOXOLM: 198.19 g/mol)

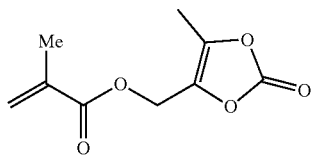

600 g (6.0 mol) of methyl methacrylate, 118 g (1.0 mol) of 4-hydroxymethyl-5-methyl-1,3-dioxolen-2-one from example 4 and 0.14 g of 4-hydroxy-2,2,6,6-tetramethylpiperidinooxyl (Tempol) are charged to a round-bottomed flask equipped with a distillation column. Any traces of water present in the medium are removed by azeotropic distillation with methyl methacrylate. The mixture is cooled slightly and 18.0 g of zirconium acetylacetonate (catalyst) are introduced and the equivalent amount of methyl methacrylate which had previously been removed by azeotropic distillation is added. The reaction medium is brought to reflux. Alcoholysis begins at around 65° C. with removal of the methanol/methyl methacrylate azeotrope and the reaction finishes at around 100° C. After the end of the alcoholysis the mixture is cooled and the zirconium acetylacetonate (catalyst) is precipitated with dilute phosphoric acid. The suspension is then filtered under pressure and the filtrate is washed with a dilute aqueous solution of NaCl to extract any traces of unreacted 4-hydroxymethyl-5-methyl-1,3-dioxolen-2-one. The residue is dried at 70° C. under reduced pressure. (5-Methyl-1,3-dioxolen-2-one-4-yl)methyl methacrylate is obtained in the form of a colorless oil with a purity of greater than 92% (88% yield).

¹H NMR (400 MHz, CDCl₃, 298 K) δ (ppm): 1.86 (s, 3H, O—C(O)—O—C(CH₃)=C—CH₂—O—C(O)—C(CH₃)=CHH), 2.31 (s, 3H, O—C(O)—O—C(CH₃)=C—CH₂—O—C(O)—C—(CH₃)=CHH), 4.72 (s, 2H, O—C(O)—O—C(CH₃)=C—CH₂—O—C(O)—C(CH₃)=CHH), 5.56 (d, 1H, O—C(O)—O—C(CH₃)=C—CH₂—O—C(O)—C(CH₃)=CHH), 6.06 (d, 1H, O—C(O)—O—C(CH₃)=C—CH₂—O—C(O)—C(CH₃)=CHH);

¹³C NMR (100 MHz, CDCl₃, 298 K) δ (ppm): 10.5 (O—C(O)—O—C(CH₃)=C—CH₂—O—C(O)—C(CH₃)=CHH), 18.4 (O—C(O)—O—C(CH₃)=C—CH₂—O—C(O)—C(CH₃)=CHH), 62.8 (O—C(O)—O—C(CH₃)=C—CH₂—O—C(O)—C(CH₃)=CHH), 126.0 (O—C(O)—O—C(CH₃)=C—CH₂—O—C(O)—C(CH₃)=CHH), 144.3 (O—C(O)—O—C(CH₃)=C—CH₂—O—C(O)—C(CH₃)=CHH), 136.1 (O—C(O)—O—C(CH₃)=C—CH₂—O—C(O)—C(CH₃)=CHH), 155.7 (O—C(O)—O—C(CH₃)=C—CH₂—O—C(O)—C(CH₃)=CHH), 153.0 (O—C(O)—O—C(CH₃)=C—CH₂—O—C(O)—C(CH₃)=CHH), 167.1 (O—C(O)—O—C(CH₃)=C—CH₂—O—C(O)—C(CH₃)=CHH).

Example 7

Preparation of glycerol carbonate methylmethacrylate (GCMM: 200.19 g/mol)

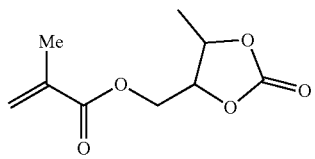

600 g (6.0 mol) of methyl methacrylate, 120 g (1.0 mol) of 4-hydroxymethyl-5-methyl-1,3-dioxolan-2-one (commercially available from Apichemical or synthesized according to JPS 60,100,571), and 0.14 g of 4-hydroxy-2,2,6,6-tetramethylpiperidinooxyl (Tempol) are charged to a round-bottomed flask equipped with a distillation column. Any traces of water present in the medium are removed by azeotropic distillation with methyl methacrylate. The mixture is cooled slightly and 18.0 g of zirconium acetylacetonate (catalyst) are introduced and the equivalent amount of methyl methacrylate which had previously been removed by azeotropic distillation is added. The reaction medium is brought to reflux. Alcoholysis begins at around 65° C. with removal of the methanol/methyl methacrylate azeotrope and the reaction finishes at around 100° C. After the end of the alcoholysis the mixture is cooled and the zirconium acetylacetonate (catalyst) is precipitated with dilute phosphoric acid. The suspension is then filtered under pressure and the filtrate is washed with a dilute aqueous solution of NaCl to extract any traces of unreacted 4-hydroxymethyl-5-methyl-1,3-dioxolen-2-one. The residue is dried at 70° C. under reduced pressure. (5-Methyl-1,3-dioxolan-2-one-4-yl) methyl methacrylate is obtained in the form of a colorless oil with a purity of greater than 93% (90% yield).

¹H NMR (400 MHz, CDCl₃, 298 K) δ (ppm): 1.86 (s, 3H, O—C(O)—O—CH(CH₃)—CH—CH₂—O—C(O)—C(CH₃)=CHH), 1.21 (d, 3H, O—C(O)—O—CH(CH₃)—CH—CH₂—O—C(O)—C(CH₃)=CHH), 4.35 (d, 2H, O—C(O)—O—CH(CH₃)—CH—CH₂—O—C(O)—C(CH₃)=CHH), 4.59 (dt, 1 H, O—C(O)—O—CH(CH₃)—CH—CH₂—O—C(O)—C(CH₃)=CHH), 4.84 (qd, 1 H, O—C(O)—O—CH(CH₃)—CH—CH₂—O—C(O)—C(CH₃)=CHH), 5.60 (d, 1H, O—C(O)—O—CH(CH₃)—CH—CH₂—O—C(O)—C(CH₃)=CHH), 6.06 (d, 1H, O—C(O)—O—CH(CH₃)=C—CH₂—O—C(O)—C(CH₃)=CHH);

¹³C NMR (100 MHz, CDCl₃, 298 K) δ (ppm): 15.9 (O—C(O)—O—CH(CH₃)—CH—CH₂—O—C(O)—C(CH₃)=CHH), 18.4 (O—C(O)—O—CH(CH₃)—CH—CH₂—O—C(O)—C(CH₃)=CHH), 66.7 (O—C(O)—O—CH(CH₃)—CH—CH₂—O—C(O)—C(CH₃)=CHH), 126.0 (O—C(O)—O—CH(CH₃)—CH—CH₂—O—C(O)—C(CH₃)=CHH), 78.0 (O—C(O)—O—CH(CH₃)—CH—CH₂—O—C(O)—C(CH₃)=CHH), 136.1 (O—C(O)—O—CH(CH₃)—CH—CH₂—O—C(O)—C(CH₃)=CHH), 81.6 (O—C(O)—O—CH(CH₃)—CH—CH₂—O—C(O)—C(CH₃)=CHH), 154.0 (O—C(O)—O—CH(CH₃)—CH—CH₂—O—C(O)—C(CH₃)=CHH), 167.1 (O—C(O)—O—CH(CH₃)—CH—CH₂—O—C(O)—C(CH₃)=CHH).

Example 8

Preparation of 2-[[[(5-methyl-1,3-dioxolen-2-one-4-yl)methoxy]carbonyl]amino]ethyl acrylate (271.21 g/mol)

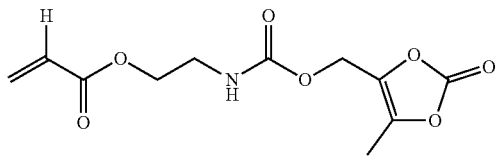

141.1 g (1.0 mol) of 2-isocyanatoethyl acrylate are loaded, heated to 60° C. and a mixture of 118 g (1.0 mol) of 4-hydroxymethyl-5-methyl-1,3-dioxolen-2-one from example 4 and 4 g of dibutyltin dilaurate (DBTL) is slowly added while maintaining the temperature between 60° C. and 80° C. After having added all of the mixture, 0.1 g of MEHQ (SIGMA-ALDRICH) is added and the reaction mixture is maintained between 70° C. and 80° C. until there are no longer any NCO functions visible in the infrared (IR) (disappearance of the characteristic band of the NCO function at about 2250 cm$^{-1}$). 2-[[[(5-Methyl-1,3-dioxolen-2-one-4-yl)methoxy]carbonyl]amino]ethyl acrylate is obtained in the form of a colorless viscous oil with a purity of greater than 98% (98% yield).

$^1$H NMR (400 MHz, CDCl$_3$, 298 K) δ (ppm): 2.31 (s, 3H, O—C(O)—O—C(CH$_3$)=C—CH$_2$—O—C(O)—NH—CH2-CH2-O—C(O)—CH=CHH), 3.46 (t, 2H, O—C(O)—O—C(CH$_3$)=C—CH$_2$—O—C(O)—NH—CH2-CH2-O—C(O)—CH=CHH), 4.42 (t, 2H, O—C(O)—O—C(CH$_3$)=C—CH$_2$—O—C(O)—NH—CH2-CH2-O—C(O)—CH=CHH), 4.72 (s, 2H, O—C(O)—O—C(CH$_3$)=C—CH$_2$—O—C(O)—NH—CH2-CH2-O—C(O)—CH=CHH), 6.02 (dd, 1H, O—C(O)—O—C(CH$_3$)=C—CH$_2$—O—C(O)—NH—CH2-CH2-O—C(O)—CH=CHH), 6.33 (dd, 1H, O—C(O)—O—C(CH$_3$)=C—CH$_2$—O—C(O)—NH—CH2-CH2-O—C(O)—CH=CHH), 6.86 (dd, 1 H, O—C(O)—O—C(CH$_3$)=C—CH$_2$—O—C(O)—NH—CH2-CH2-O—C(O)—CH=CHH).

$^{13}$C NMR (100 MHz, CDCl$_3$, 298 K) δ (ppm): 10.5 (O—C(O)—O—C(CH$_3$)=C—CH$_2$—O—C(O)—NH—CH2-CH2-O—C(O)—CH=CHH), 40.5 (O—C(O)—O—C(CH$_3$)=C—CH$_2$—O—C(O)—NH—CH2-CH2-O—C(O)—CH=CHH), 61.0 (O—C(O)—O—C(CH$_3$)=C—CH$_2$—O—C(O)—NH—CH2-CH2-O—C(O)—CH=CHH), 62.8 (O—C(O)—O—C(CH$_3$)=C—CH$_2$—O—C(O)—NH—CH2-CH2-O—C(O)—CH=CHH), 128.0 (O—C(O)—O—C(CH$_3$)=C—CH$_2$—O—C(O)—NH—CH2-CH2-O—C(O)—CH=CHH), 131.1 (O—C(O)—O—C(CH$_3$)=C—CH$_2$—O—C(O)—NH—CH2-CH2-O—C(O)—CH=CHH), 144.3 (O—C(O)—O—C(CH$_3$)=C—CH$_2$—O—C(O)—NH—CH2-CH2-O—C(O)—CH=CHH), 153.0 (O—C(O)—O—C(CH$_3$)=C—CH$_2$—O—C(O)—NH—CH2-CH2-O—C(O)—CH=CHH), 155.7 (O—C(O)—O—C(CH$_3$)=C—CH$_2$—O—C(O)—NH—CH2-CH2-O—C(O)—CH=CHH), 156.3 (O—C(O)—O—C(CH$_3$)=C—CH$_2$—O—C(O)—NH—CH2-CH2-O—C(O)—CH=CHH), 166.1 (O—C(O)—O—C(CH$_3$)=C—CH$_2$—O—C(O)—NH—CH2-CH2-O—C(O)—CH=CHH).

Example 9

Preparation of 2-[[[(5-methyl-1,3-dioxolen-2-one-4-yl)methoxy]carbonyl]amino]ethyl methacrylate (285.24 g/mol)

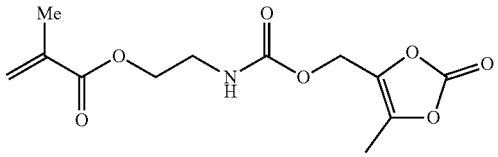 [SMILES: C=CC(=O)OCCNC(=O)OCc1oc(=O)oc1C]

155.2 g (1.0 mol) of 2-isocyanatoethyl methacrylate are loaded, heated to 60° C. and a mixture of 118 g (1.0 mol) of 4-hydroxymethyl-5-methyl-1,3-dioxolen-2-one from example 4 and 4 g of dibutyltin dilaurate (DBTL) is slowly added while maintaining the temperature between 60° C. and 80° C. After having added all of the mixture, 0.1 g of MEHQ (SIGMA-ALDRICH) is added and the reaction mixture is maintained between 70° C. and 80° C. until there are no longer any NCO functions visible in the infrared (IR) (disappearance of the characteristic band of the NCO function at about 2250 cm$^{-1}$). 2-[[[(5-Methyl-1,3-dioxolen-2-one-4-yl)methoxy]carbonyl]amino]ethyl methacrylate is obtained in the form of a colorless viscous oil with a purity of greater than 98% (98% yield).

$^1$H NMR (400 MHz, CDCl$_3$, 298 K) δ (ppm): 1.86 (s, 3H, O—C(O)—O—C(CH$_3$)=C—CH$_2$—O—C(O)—NH—CH2-CH2-O—C(O)—C(CH$_3$)=CHH); 2.31 (s, 3H, O—C(O)—O—C(CH$_3$)=C—CH$_2$—O—C(O)—NH—CH2-CH2-O—C(O)—C(CH$_3$)=CHH), 3.46 (t, 3H, O—C(O)—O—C(CH$_3$)=C—CH$_2$—O—C(O)—NH—CH2-CH2-O—C(O)—C(CH$_3$)=CHH), 4.42 (t, 2H, O—C(O)—O—C(CH$_3$)=C—CH$_2$—O—C(O)—NH—CH2-CH2-O—C(O)—C(CH$_3$)=CHH), 4.72 (s, 2H, O—C(O)—O—C(CH$_3$)=C—CH$_2$—O—C(O)—NH—CH2-CH2-O—C(O)—C(CH$_3$)=CHH), 5.56 (dd, 1H, O—C(O)—O—C(CH$_3$)=C—CH$_2$—O—C(O)—NH—CH2-CH2-O—C(O)—C(CH3)=CHH), 6.05 (dd, 1H, O—C(O)—O—C(CH$_3$)=C—CH$_2$—O—C(O)—NH—CH2-CH2-O—C(O)—C(CH$_3$)=CHH).

$^{13}$C NMR (100 MHz, CDCl$_3$, 298 K) δ (ppm): 10.5 (O—C(O)—O—C(CH$_3$)=C—CH$_2$—O—C(O)—NH—CH2-CH2-O—C(O)—C(CH3)=CHH), 18.4 (O—C(O)—O—C(CH$_3$)=C—CH$_2$—O—C(O)—NH—CH2-CH2-O—C(O)—C(CH$_3$)=CHH), 40.5 (O—C(O)—O—C(CH$_3$)=C—CH$_2$—O—C(O)—NH—CH2-CH2-O—C(O)—C(CH$_3$)=CHH), 61.0 (O—C(O)—O—C(CH$_3$)=C—CH$_2$—O—C(O)—NH—CH2-CH2-O—C(O)—C(CH$_3$)=CHH), 62.8 (O—C(O)—O—C(CH$_3$)=C—CH$_2$—O—C(O)—NH—CH2-CH2-O—C(O)—C(CH$_3$)=CHH), 126.0 (O—C(O)—O—C(CH$_3$)=C—CH$_2$—O—C(O)—NH—CH2-CH2-O—C(O)—C(CH$_3$)=CHH), 136.1 (O—C(O)—O—C(CH$_3$)=C—CH$_2$—O—C(O)—NH—CH2-CH2-O—C(O)—C(CH$_3$)=CHH), 144.3 (O—C(O)—O—C(CH$_3$)=C—CH$_2$—O—C(O)—NH—CH2-CH2-O—C(O)—C(CH$_3$)=CHH), 155.7 (O—C(O)—O—C(CH$_3$)=C—CH$_2$—O—C(O)—NH—CH2-CH2-O—C(O)—C(CH$_3$)=CHH), 156.3 (O—C(O)—O—C(CH$_3$)=C—CH$_2$—O—

C(O)—NH—CH2-CH2-O—C(O)—C(CH$_3$)=CHH), 153.0 (O—C(O)—O—C(CH$_3$)=C—CH$_2$—O—C(O)—NH—CH2-CH2-O—C(O)—C(CH$_3$)=CHH), 167.6 (O—C(O)—O—C(CH$_3$)=C—CH$_2$—O—C(O)—NH—CH2-CH2-O—C(O)—C(CH$_3$)=CHH).

B. Synthesis of the Copolymers

1) Raw Materials Used (Table 1)

TABLE 1

| Chemical name or trade name of product | Abbreviated name in description | Supplier | Function |
|---|---|---|---|
| Styrene | STY | Total | Monoethylenically unsaturated monomer |
| Butyl acrylate | BuA | Arkema | Monoethylenically unsaturated monomer |
| Methyl methacrylate | MMA | Arkema | Monoethylenically unsaturated monomer |
| 4-methacryloyloxymethyl-1,3-dioxolan-2-one (glycerol carbonate methacrylate) | GCM** | / | Monomer |
| 4-methacryloyloxymethyl-5-methyl-1,3-dioxolan-2-one (glycerol carbonate methyl methacrylate) | GCMM | Example 7 | Monomer |
| (5-methyl-1,3-dioxolen-2-one-4-yl) methyl methacrylate | DIOXOLM | Example 6 | Monomer of formula (I) |
| Isobornyl methacrylate | MAISOBOR | Evonik | Monoethylenically unsaturated monomer |
| Luperox ® DI | DTBP | Arkema | Initiator |
| Luperox ® 26 | TBPO | Arkema | Initiator |
| Ektapro ® EEP (ethyl 3-ethoxypropionate) | EEP | Aldrich | Solvent |

**GCM: obtained according to example 1 of U.S. Pat. No. 7,414,147

2) Preparation of the Copolymers

Example 10

Copolymer According to the Invention

Ethyl 3-ethoxypropionate (EEP, 218 g) is introduced into a 2000 mL reactor. Under nitrogen flushing, the reactor is brought to 150° C. At the same time, 148 g of styrene, 124 g of butyl acrylate, 9.8 g of methyl methacrylate, 254 g of (5-methyl-1,3-dioxolen-2-one-4-yl)methyl methacrylate (example 6) and 130 g of isobornyl methacrylate are mixed. At the same time, a solution of di-tert-butyl peroxide DTBP (24.7 g) and tert-butyl peroctoate TBPO (9.8 g) in ethyl 3-ethoxypropionate (EEP, 47 g) is also prepared. These two preparations are then introduced simultaneously into the reactor over a period of 7 h 30 min, the temperature being maintained at 150° C. throughout this period under nitrogen flushing. At the end of these additions, the medium is maintained at the same temperature for 1 h before being cooled to room temperature.

The final solids content of the polymer is then 71% and its viscosity, measured at 25° C. according to the ISO3219 standard, is 13.1 Pa·s.

Example 11

Comparative Example

Ethyl 3-ethoxypropionate (218 g) is introduced into a 2000 mL reactor. Under nitrogen flushing, the reactor is brought to 150° C. At the same time, 148 g of styrene, 124 g of butyl acrylate, 9.8 g of methyl methacrylate, 239 g of glycerol carbonate methacrylate (GCM) and 130 g of isobornyl methacrylate are mixed. At the same time, a solution of di-tert-butyl peroxide DTBP (24.7 g) and tert-butyl peroctoate TBPO (9.8 g) in ethyl 3-ethoxypropionate (47 g) is also prepared. These two preparations are then introduced simultaneously into the reactor over a period of 7 h 30 min, the temperature being maintained at 150° C. throughout this period under nitrogen flushing. At the end of these additions, the medium is maintained at the same temperature for 1 h before being cooled to room temperature.

The final solids content of the polymer is then 70% and its viscosity, measured at 25° C. according to the ISO3219 standard, is 12.5 Pa·s.

Example 12

Comparative Example

Ethyl 3-ethoxypropionate (218 g) is introduced into a 2000 mL reactor. Under nitrogen flushing, the reactor is brought to 150° C. At the same time, 148 g of styrene, 124 g of butyl acrylate, 9.8 g of methyl methacrylate, 241 g of glycerol carbonate methyl methacrylate (GCMM, example 7) and 130 g of isobornyl methacrylate are mixed. At the same time, a solution of di-tert-butyl peroxide DTBP (24.7 g) and tert-butyl peroctoate TBPO (9.8 g) in ethyl 3-ethoxypropionate (47 g) is also prepared. These two preparations are then introduced simultaneously into the reactor over a period of 7 h 30 min, the temperature being maintained at 150° C. throughout this period under nitrogen flushing. At the end of these additions, the medium is maintained at the same temperature for 1 h before being cooled to room temperature.

The final solids content of polymer is then 70% and its viscosity, measured at 25° C. according to the ISO3219 standard, is 13.0 Pa·s.

The compositions of the monomer mixtures used in examples 10, 11 and 12 have been grouped together in table 2 below:

TABLE 2

| Composition (% by weight) | Example 10 (invention) | Example 11 (comparative) | Example 12 (comparative) |
|---|---|---|---|
| STY | 22.2 | 22.7 | 22.1 |
| BuA | 18.6 | 19.1 | 18.5 |
| MMA | 1.5 | 1.5 | 1.5 |
| DIOXOLM | 38.2 | — | — |
| GCMM | — | — | 38.5 |
| GCM | — | 36.7 | — |
| MAISOBOR | 19.5 | 20.0 | 19.4 |
| Functionality** (meq/g) | 1.93 | 1.97 | 1.93 |
| Solids content (% by weight) | 71 | 70 | 71 |
| Viscosity at 25° C. according to ISO 2884-1 (Pa · s) | 13.1 | 12.5 | 13.0 |

**Solvated polymer

C. Preparation of the Compositions

The preparations used in example 10 (invention) and in examples 11 and 12 (comparative) have been grouped together in table 3 below:

TABLE 3

| | Composition C1 (invention) | Composition C2 (comparative) | Composition C3 (comparative) |
|---|---|---|---|
| Polymer from example 10 (71% solids content) | 50.00 g | — | — |
| Polymer from example 11 (70% solids content) | — | 50.00 g | — |
| Polymer from example 12 (70% solids content) | — | — | 50.00 g |
| Ethylene diamine | 2.07 g | 2.11 g | 2.07 g |
| Butyl acetate (solvent) | 9.50 g | 9.50 g | 9.50 g |
| Viscosity at 25° C. according to ISO 2884-1 (mPa · s) | 300 | 290 | 298 |
| Density at 20° C. according to ISO 2811 | 1.04 | 1.03 | 1.04 |
| Solids content according to ISO 3251 (%) | 57.7 | 56.9 | 57.5 |

The general procedure for mixing the compositions is as follows:

The amounts of polymer and amino compound as indicated in table 3 are poured into a cylindrical container. The medium is then stirred at room temperature (23° C.) with a Dispermat® CV planetary mixer. This mixture is then diluted with butyl acetate in order to obtain a high-gradient viscosity at 25° C. of 290±20 mPa·s enabling the application of the composition on a QD46-type steel support with a Barecoater applicator (speed 3=20 mm/s) in order to obtain a dry basis weight of 30 to 40 μm.

1) Dust-Free Drying Test According to ISO 1517

The principle is as follows: using fine calibrated glass beads (particle size 125/250 μm), the moment from which they no longer remain bonded to the support covered with crosslinkable composition C1, C2 or C3 is determined. The support covered with crosslinkable composition C1, C2 or C3 is placed in the air-conditioned room (23° C./50% RH). After a certain time, at the end of which it is considered that the composition has sufficiently reacted, a spatula-full of glass beads (around 0.5 g) is withdrawn and they are poured onto the support covered with crosslinkable composition C1, C2 or C3 using a small tube 10 cm high. After 10 seconds, the support is inclined by 20° and the glass beads are removed using a fine brush. If they do not remain bonded, the dry coating is considered to be "dust-free" at the corresponding drying time (after application). In the contrary case, another test is performed a few minutes later and so on until no beads stick to the surface of the coating in order to note the dust-free drying time.

2) Hardness Test According to the ISO 1522 Method

This is a Persoz hardness carried out at 23° C. and 50% relative humidity. The coatings are applied to QD36-type steel (Q-Panel) then left under the conditions described above (23° C. and 50% relative humidity) for a period of 7 days. The measurements are taken after 1 day, 4 days and 7 days of drying.

3) Performance of the Crosslinked Compositions

The application performance of composition C1 and of comparative compositions C2 and C3 after crosslinking have been grouped together in table 4 below.

TABLE 4

| | Composition C1 | Composition C2 | Composition C3 |
|---|---|---|---|
| Dry film thickness (μm) | 35 ± 1 | 35 ± 1 | 35 ± 1 |
| Dust-free drying | 0h58 | 1h00 | 1h05 |
| Persoz hardness 1 day | 150 | 110 | 90 |
| Persoz hardness 4 days | 200 | 180 | 160 |
| Persoz hardness 7 days | 200 | 195 | 180 |
| Persoz hardness 8 days | 200 | 195 | 196 |

It is observed that, under the same test conditions, composition C1 according to the invention advantageously makes it possible to achieve the desired final Persoz hardness in only 4 days instead of the 7 days observed for comparative composition C2, and instead of more than 8 days for comparative composition C3.

The invention claimed is:

1. A monoethylenically unsaturated monomer M having the formula (I) below:

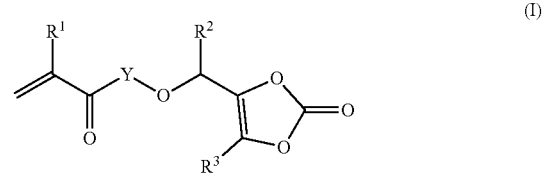

wherein:
$R^1$ represents a hydrogen atom or a methyl radical;
$R^2$ represents a hydrogen atom, a linear or branched alkyl radical comprising from 1 to 10 carbon atoms, a cycloalkyl radical comprising from 3 to 10 carbon atoms, an aryl radical or an arylalkyl radical;
$R^3$ represents a hydrogen atom, a linear or branched alkyl radical comprising from 1 to 10 carbon atoms, a cycloalkyl radical comprising from 3 to 10 carbon atoms, an aryl radical or an arylalkyl radical;
or $R^2$ and $R^3$ may be bonded together to form a $-(CH_2-)_p-$ group with p being an integer ranging from 3 to 5;

Y represents a bond or a —$X_1$—$(CH_2)_n$—$X_2$— radical with:
- $X_1$ represents O, S, NH or NR' with R' representing an alkyl radical;
- $X_2$ represents NHC(O) or C(O);
- n represents an integer ranging from 2 to 10.

2. The monomer M as claimed in claim 1, being chosen from the monomers of formula (I-1) or of formula (I-2) below:

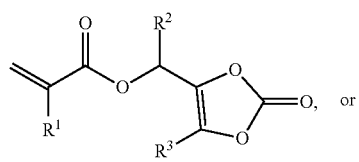
(I-1)

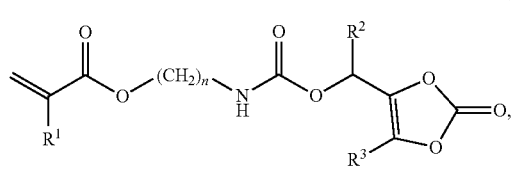
(I-2)

wherein $X_1$, $X_2$, n, $R^1$, $R^2$ and $R^3$ are as defined in claim 1.

3. The monomer M as claimed in claim 1, wherein
$R^2$ represents a hydrogen atom; and/or
$R^3$ represents a linear or branched alkyl radical comprising from 1 to 10 carbon atoms.

4. A process for preparing the monomer M of claim 1, comprising using a compound of formula (II) below to prepare the monomer M:

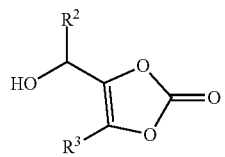
(II)

wherein
$R^2$ represents a hydrogen atom, a linear or branched alkyl radical comprising from 1 to 10 carbon atoms, a cycloalkyl radical comprising from 3 to 10 carbon atoms, an aryl radical or an arylalkyl radical;
$R^3$ represents a hydrogen atom, a linear or branched alkyl radical comprising from 1 to 10 carbon atoms, a cycloalkyl radical comprising from 3 to 10 carbon atoms, an aryl radical or an arylalkyl radical;
or $R^2$ and $R^3$ may be bonded together to form a —$(CH_2)_p$— group with p being an integer ranging from 3 to 5.

5. A process for preparing the monomer M of formula (I-1) as defined in claim 2, comprising reacting a compound of formula (II):

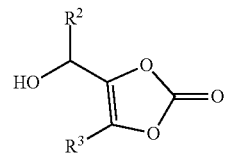
(II)

wherein
$R^2$ represents a hydrogen atom, a linear or branched alkyl radical comprising from 1 to 10 carbon atoms, a cycloalkyl radical comprising from 3 to 10 carbon atoms, an aryl radical or an arylalkyl radical;
$R^3$ represents a hydrogen atom, a linear or branched alkyl radical comprising from 1 to 10 carbon atoms, a cycloalkyl radical comprising from 3 to 10 carbon atoms, an aryl radical or an arylalkyl radical;
or $R^2$ and $R^3$ may be bonded together to form a —$(CH_2)_p$— group with p being an integer ranging from 3 to 5;
with a compound of formula (III):

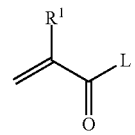
(III)

wherein:
$R^1$ represents a hydrogen atom or a methyl radical, and
L represents a leaving group, for example a radical chosen from the group consisting of halogens, hydroxyl (OH) groups and alkoxy groups comprising from 1 to 10 carbon atoms.

6. A process for preparing the monomer M of formula (I-2) as defined in claim 2, comprising reacting a compound of formula (II):

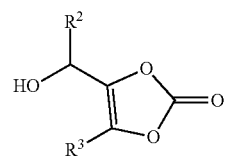
(II)

wherein
$R^2$ represents a hydrogen atom, a linear or branched alkyl radical comprising from 1 to 10 carbon atoms, a cycloalkyl radical comprising from 3 to 10 carbon atoms, an aryl radical or an arylalkyl radical;
$R^3$ represents a hydrogen atom, a linear or branched alkyl radical comprising from 1 to 10 carbon atoms, a cycloalkyl radical comprising from 3 to 10 carbon atoms, an aryl radical or an arylalkyl radical;
or $R^2$ and $R^3$ may be bonded together to form a —$(CH_2)_p$— group with p being an integer ranging from 3 to 5;

with a compound having the general formula (IV) below:

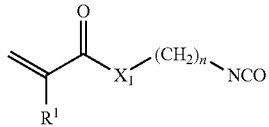

(IV)

wherein

R¹ represents a hydrogen atom or a methyl radical,

X₁ represents O, S, NH or NR' with R' representing an alkyl radical; and n represents an integer ranging from 2 to 10.

7. A polymer comprising at least one repeating unit of general formula (V) below:

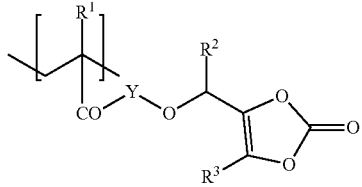

(V)

wherein

R¹ represents a hydrogen atom or a methyl radical;

R² represents a hydrogen atom, a linear or branched alkyl radical comprising from 1 to 10 carbon atoms, a cycloalkyl radical comprising from 3 to 10 carbon atoms, an aryl radical or an arylalkyl radical;

R³ represents a hydrogen atom, a linear or branched alkyl radical comprising from 1 to 10 carbon atoms, a cycloalkyl radical comprising from 3 to 10 carbon atoms, an aryl radical or an arylalkyl radical;

or R² and R³ may be bonded together to form a —(CH₂—)$_p$— group with p being an integer ranging from 3 to 5;

Y represents a bond or a —X₁—(CH₂)$_n$—X₂— radical with:

X₁ represents O, S, NH or NR' with R' representing an alkyl radical;

X₂ represents NHC(O) or C(O);

n represents an integer ranging from 2 to 10.

8. The polymer of claim 7, wherein the repeating unit of formula (V) is chosen from the repeating units of formula (V-a) or (V-b) below:

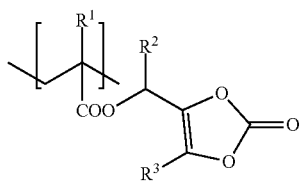

(V-a)

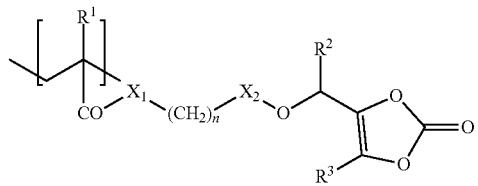

(V-b)

wherein

R¹ represents a hydrogen atom or a methyl radical;

R² represents a hydrogen atom, a linear or branched alkyl radical comprising from 1 to 10 carbon atoms, a cycloalkyl radical comprising from 3 to 10 carbon atoms, an aryl radical or an arylalkyl radical;

R³ represents a hydrogen atom, a linear or branched alkyl radical comprising from 1 to 10 carbon atoms, a cycloalkyl radical comprising from 3 to 10 carbon atoms, an aryl radical or an arylalkyl radical;

or R² and R³ may be bonded together to form a —(CH₂—)$_p$— group with p being an integer ranging from 3 to 5;

X₁ represents O, S, NH or NR' with R' representing an alkyl radical;

X₂ represents NHC(O) or C(O);

n represents an integer ranging from 2 to 10.

9. A process for preparing a polymer, comprising a step of polymerizing at least one monomer M as claimed in claim 1, optionally in the presence of at least one ethylenically unsaturated monomer different from the at least one monomer M.

10. The process as claimed in claim 9, wherein the at least one ethylenically unsaturated monomer different from the monomer M is chosen from monoethylenically unsaturated monomers (monomers B), and/or multiethylenically unsaturated monomers (monomers C), said monomers B being chosen from the following families:

B1: Monoethylenically unsaturated C3 to C8 carboxylic acids and monoethylenically unsaturated C4 to C8 dicarboxylic acids;

B2: Monoethylenically unsaturated C3 to C8 carboxylic acid amides and monoethylenically unsaturated C4 to C8 dicarboxylic acid diamides;

B3: Monoethylenically unsaturated C4 to C8 acid anhydrides;

B4: Esters of monoethylenically unsaturated C3 to C8 carboxylic acids and C2 to C4 alcohols and equivalents thereof based on monoethylenically unsaturated C4 to C8 dicarboxylic acids;

B5: Monoethylenically unsaturated sulfonic acids (and also the alkali metal or ammonium salts thereof);

B6: Monoethylenically unsaturated C3 to C5 nitriles;

B7: Heterocyclic N-vinyl derivatives;

B8: Monoethylenically unsaturated compounds comprising a C2 (EO), C3 (PO) and C4 (BO) poly(alkylene oxide) group, and also the corresponding esters of monoethylenically unsaturated C3 to C8 carboxylic acids and monoethylenically unsaturated dicarboxylic acids with glycols and C2 (EO), C3 (PO) and C4 (BO) poly(alkylene glycol)s derived from C1 to C14 alcohols;

B9: Vinyl aromatic derivatives;

B10: Esters of monoethylenically unsaturated C3 to C8 carboxylic acids and of C1 to C20 alcohols, of C5 to C8 cyclic alcohols, of C1 to C4 alcohols comprising a phenyl group or of C1 to C4 alcohols comprising a phenoxy group;

B11: Diesters of monoethylenically unsaturated C4 to C8 acids and of C1 to C20 alcohols, of C5 to C8 cycloalkanols, of C1 to C4 alcohols comprising a phenyl group or of C1 to C4 alcohols comprising a phenoxy group;

B12: Alkylamides and dialkylamides of monoethylenically unsaturated C3 to C8 carboxylic acids and of C1 to C20 primary or secondary amines;

B13: Vinyl esters of C1 to C20 atom aliphatic carboxylic acids;

B14: Conjugated and unsaturated C4 to C10 olefins;

B15: C2 to C20 olefins;

B16: C2 to C20 olefins substituted with a halogen atom;

B17: Monoethylenically unsaturated monomers having one or two epoxy groups;

B18: Monoethylenically unsaturated monomers comprising at least one carbonate group;

B19: Esters of monoethylenically unsaturated C3 to C8 carboxylic acids or monoethylenically unsaturated C4 to C8 dicarboxylic acids with C8 to C24 unsaturated alcohols or C8 to C24 unsaturated diols;

B20: Esters of monoethylenically unsaturated C3 to C8 carboxylic acids or of monoethylenically unsaturated C4 to C8 dicarboxylic acids bearing an alkoxysilane group chosen from trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl methacrylate, triethoxysilylpropyl methacrylate, tributoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, trimethoxysilylpropyl acrylate, triethoxysilylpropyl acrylate, or tributoxysilylpropyl acrylate;

B21: Monoethylenically unsaturated monomers comprising phosphonates chosen from N-methacrylamidomethylphosphonic acid ester derivatives, and the phosphonic monoacid and diacid derivatives thereof; N-methacrylamidoethylphosphonic acid ester derivatives, and the phosphonic monoacid and diacid derivatives thereof; N-acrylamidomethylphosphonic acid ester derivatives, and the phosphonic monoacid and diacid derivatives thereof; vinylbenzylphosphonate dialkyl ester derivatives, and the phosphonic monoacid and diacid variants thereof; dialkylphosphonoalkyl acrylates and methacrylates, and the phosphonic monoacid and diacid variants thereof; vinylphosphonic acid, optionally substituted by cyano, phenyl, ester or acetate groups, vinylidenephosphonic acid, in the form of sodium salt or the isopropyl ester thereof, bis(2-chloroethyl) vinylphosphonate, it being possible for these monomers having a phosphonic monoacid or diacid function to be used in the partially or completely neutralized form, optionally neutralized by an amine, for example dicyclohexylamine;

B22: monoethylenically unsaturated monomers chosen from the phosphate analogs of the phosphonate monomers described above, the monomers then comprising a —C—O—P— sequence in comparison with the —C—P— sequence of the phosphonates;

B23: monoethylenically unsaturated monomers comprising at least one boronate function or a precursor alone or as mixtures, or in the form of salts;

B24: amides of vinylamine;

B25: monoethylenically unsaturated monomers comprising a tertiary amino group, or a heterocyclic group containing nitrogen or zwitterionic monomers.

11. The polymer of claim 7, wherein it is a copolymer comprising:

at least one repeating unit of general formula (V) below:

wherein $R^1$ represents a hydrogen atom or a methyl radical;

$R^2$ represents a hydrogen atom, a linear or branched alkyl radical comprising from 1 to 10 carbon atoms, a cycloalkyl radical comprising from 3 to 10 carbon atoms, an aryl radical or an arylalkyl radical;

$R^3$ represents a hydrogen atom, a linear or branched alkyl radical comprising from 1 to 10 carbon atoms, a cycloalkyl radical comprising from 3 to 10 carbon atoms, an aryl radical or an arylalkyl radical;

or $R^2$ and $R^3$ may be bonded together to form a —(CH$_2$—)$_p$— group with p being an integer ranging from 3 to 5;

Y represents a bond or a —X$_1$—(CH$_2$)$_n$—X$_2$— radical with:

X$_1$ represents O, S, NH or NR' with R' representing an alkyl radical;

X$_2$ represents NHC(O) or C(O);

n represents an integer ranging from 2 to 10; and at least one repeating unit resulting from the polymerization of at least one monomer B chosen from the following monomers:

B9: Vinyl aromatic derivatives;

B10: Esters of monoethylenically unsaturated C3 to C8 carboxylic acids and of C1 to C20 alcohols, of C5 to C8 cyclic alcohols, of C1 to C4 alcohols comprising a phenyl group or of C1 to C4 alcohols comprising a phenoxy group;

and mixtures thereof.

12. A composition comprising:

a composition A comprising at least one polymer as claimed in claim 7; and a composition B comprising at least one compound C comprising at least two functional groups F, which are identical or different.

13. The composition as claimed in claim 12, wherein the amount of compound(s) C is chosen so that the molar ratio of functions of formula (A):functional groups F of the compound(s) C is between 1:10 and 10:1.

14. The composition as claimed in claim 12, wherein the compound C is chosen from amino compounds, alcoholic compounds, amino acids, and mixtures thereof.

15. The composition as claimed in claim 14, wherein the amino compounds are chosen from aliphatic polyamines, cycloaliphatic polyamines, aromatic polyamines, arylaliphatic polyamines, polymeric amines, polyamidoamines, polyetheramines, and mixtures thereof.

* * * * *